Figure 1:
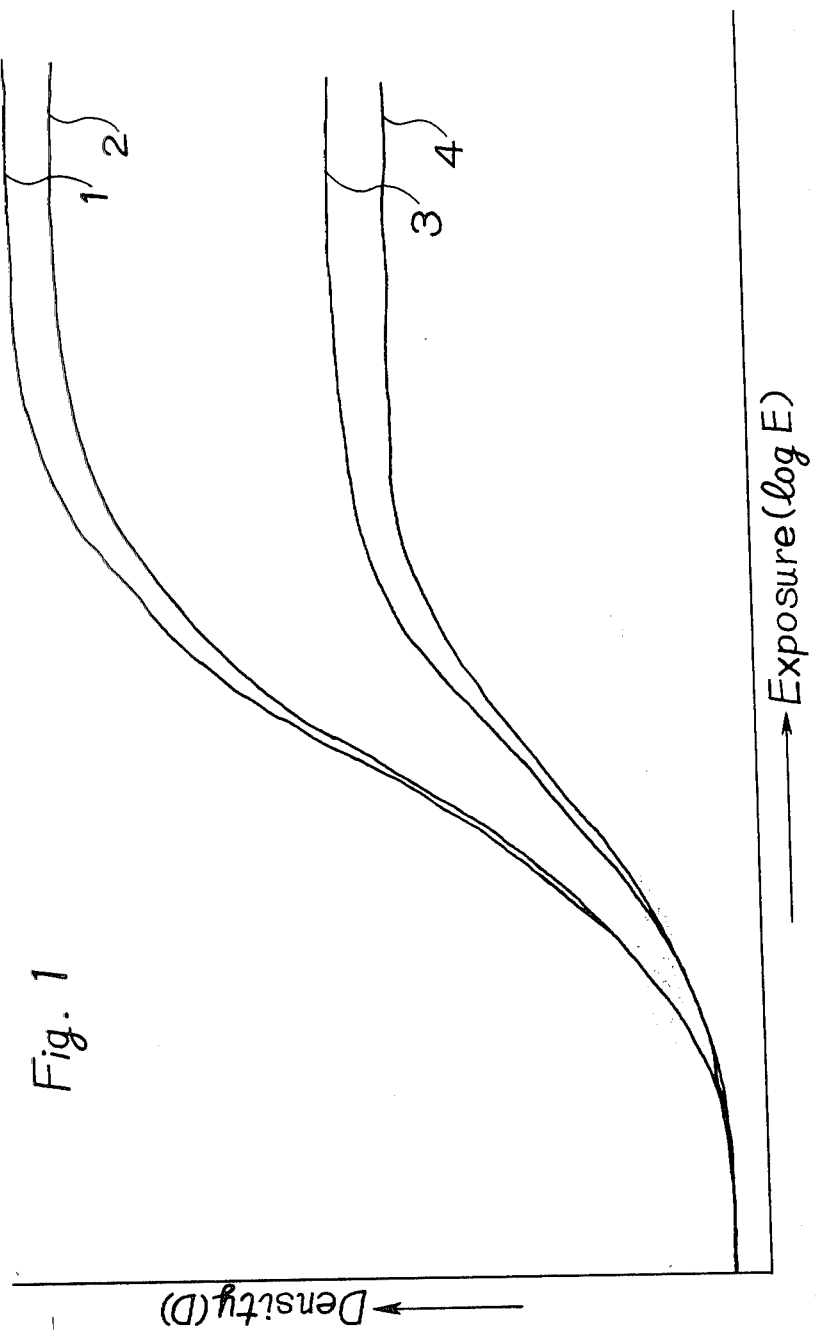

United States Patent [19]

Fujimatsu et al.

[11] 4,304,845

[45] Dec. 8, 1981

[54] SILVER HALIDE PHOTOGRAPHIC MATERIALS CONTAINING PHOTOGRAPHIC YELLOW COUPLER

[75] Inventors: Wataru Fujimatsu; Shui Sato; Tamotsu Kojima; Shigemasa Itoh; Takaya Endo, all of Hino, Japan

[73] Assignee: Konishiroku Photo Industry Co., Ltd., Tokyo, Japan

[21] Appl. No.: 161,583

[22] Filed: Jun. 20, 1980

Related U.S. Application Data

[63] Continuation of Ser. No. 953,257, Oct. 20, 1978, abandoned, which is a continuation of Ser. No. 489,031, Jul. 15, 1974, abandoned.

[30] Foreign Application Priority Data

Jul. 16, 1973 [JP] Japan .................................. 48-79309

[51] Int. Cl.$^3$ .......................... G03C 7/00; G03C 1/40
[52] U.S. Cl. .................................... 430/389; 430/472; 430/475; 430/476; 430/557; 430/558
[58] Field of Search ............... 430/375, 376, 389, 475, 430/476, 557, 558

[56] References Cited

U.S. PATENT DOCUMENTS 4,008,086  2/1977  Fujimatsu et al. .................. 430/389
4,046,575  9/1977  Boie et al. ........................... 430/558

*Primary Examiner*—J. Travis Brown
*Attorney, Agent, or Firm*—Bierman & Bierman

[57] ABSTRACT

The present invention relates to a process for forming a yellow color image which requires contacting exposed silver halide grain with a developer in the presence of a particular yellow coupler.

10 Claims, 2 Drawing Figures

SILVER HALIDE PHOTOGRAPHIC MATERIALS CONTAINING PHOTOGRAPHIC YELLOW COUPLER

This is a Continuation Application of Ser. No. 953,257 filed on Oct. 20, 1978, now abandoned, which is in turn a Continuation Application of Ser. No. 489,031, now abandoned, filed on July 15, 1974, both of which claim the priority of Japanese Patent Application No. 79309/1973 filed on July 16, 1973.

This invention relates to a yellow image-forming novel coupler for use in color photography.

It is well known in color photography that a photographic material containing couplers is exposed and then subjected to color development using a developer containing an aromatic primary amine type developing agent to form a dye image. Among the couplers used in color photography, the yellow coupler has an active methylene group which serves to form a yellow dye by coupling with oxidation product of the aromatic primary amine type developing agent. In case the active methylene group is unsubstituted, i.e. in case the coupler is a yellow coupler having its active point unsubstituted, 4 molecules of silver halide are required for forming 1 molecule of dye at the time of color development. This is the reason why the said coupler is called a 4-equivalent yellow coupler.

On the other hand, it is well known that as in the case of the unsubstituted type yellow coupler, a yellow dye is formed also from a yellow coupler, in which one of hydrogen atoms of the active methylene group thereof has been substituted by a halogen atom or the like substituent (i.e. a so-called substituted type yellow coupler). In this case, the halogen atom or the like substituent is released during the course of color development reaction, and 1 molecule of dye can be formed from 2 molecules of developed silver halide. For this reason, the substituted type yellow coupler is called a 2-equivalent yellow coupler in contrast to the aforesaid 4-equivalent yellow coupler.

When compared with the 4-equivalent yellow coupler, the 2-equivalent yellow coupler has the following advantages:

(1) The 2-equivalent yellow coupler is high in coupling rate than the 4-equivalent yellow coupler, and hence is suitable for high temperature quick treatment, particularly for 3 bath-treatment comprising the steps of only developement, bleaching, fixing and water-washing.

(2) The 2-equivalent yellow coupler requires silver halide in one-half the amount required for formation of same dye in the case of the 4-equivalent yellow coupler, and thus the cost can be reduced.

(3) When the 2-equivalent yellow coupler is used, the emulsion layer can be made thinner, and thus the resulting color image is enhanced in resolution and sharpness.

(4) When the 2-equivalent yellow coupler is used in a multi-layered photographic material, the photographic material is enhanced in light transmission to lower layers and improved in photographic speed.

Because of its having such advantages as mentioned above, the substituted type yellow coupler is extremely useful for photography.

However, conventional substituted type yellow couplers have disadvantages in that they tend to form a fog and the like color stains or to disturb development of photographic materials. In contrast thereto, the substituted type yellow coupler of the present invention is colorless and high in reactivity and scarcely forms color stains. Moreover, the yellow dye formed therefrom by color development is excellent in fastness to light, humidity, heat and pressure, has no unnecessary absorptions in the long wavelength region, shows a sharp absorption with less absorption in the green light region, and has a hue which is extremely desirable for color reproduction.

The substituted type photographic yellow coupler of the present invention is represented by the general formula;

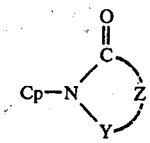

wherein Cp is a residue formed by removing one hydrogen atom of the active methylene group of a yellow coupler having an active methylene group; Y is an oxygen, sulfur or nitrogen atom, or a carbon atom having no oxygen atom bonded through double bond; and Z is a non-metallic atom grouping necessary to complete an unsaturated 5- or 6-membered heterocyclic ring together with the carbon atom, the nitrogen atom and Y, provided that Z cannot be solely carbon atoms when Y is a nitrogen atom or is a carbon atom having no oxygen atom bonded through double bond, and when Z forms an unsaturated 6-membered heterocyclic ring together with the carbon atom, the nitrogen atom and such Y. The yellow coupler of the invention is characterized in that it has in the active point thereof an unsaturated 5- or 6-membered heterocyclic ring such as a pyrimidone, pyrazone, triazone, tetrazine-one, pyrrolone, imidazolone, pyrazolone, triazolone, tetrazolone, oxazolone, isoxazolone, oxadiazolone, thiazolone, isothiazolone or thiadiazolone ring, which may have such substituent as, for example, a halogen atom or an alkyl, alkoxy, aralkyl, aryl, aryloxy, carboxyl, acyl, amino or acylamino group, or a group having a condensed ring. Concrete examples of such substituent are as follows:

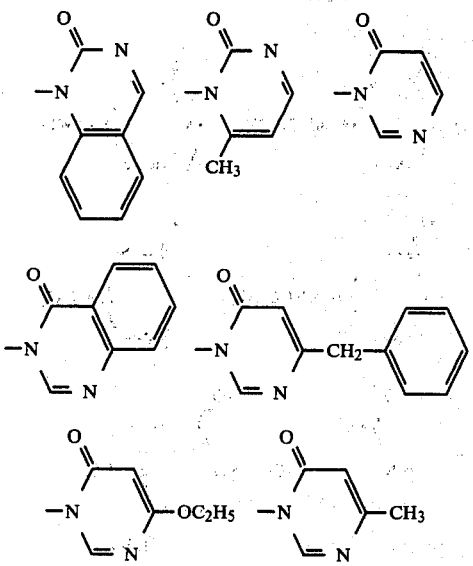

4,304,845
3
-continued
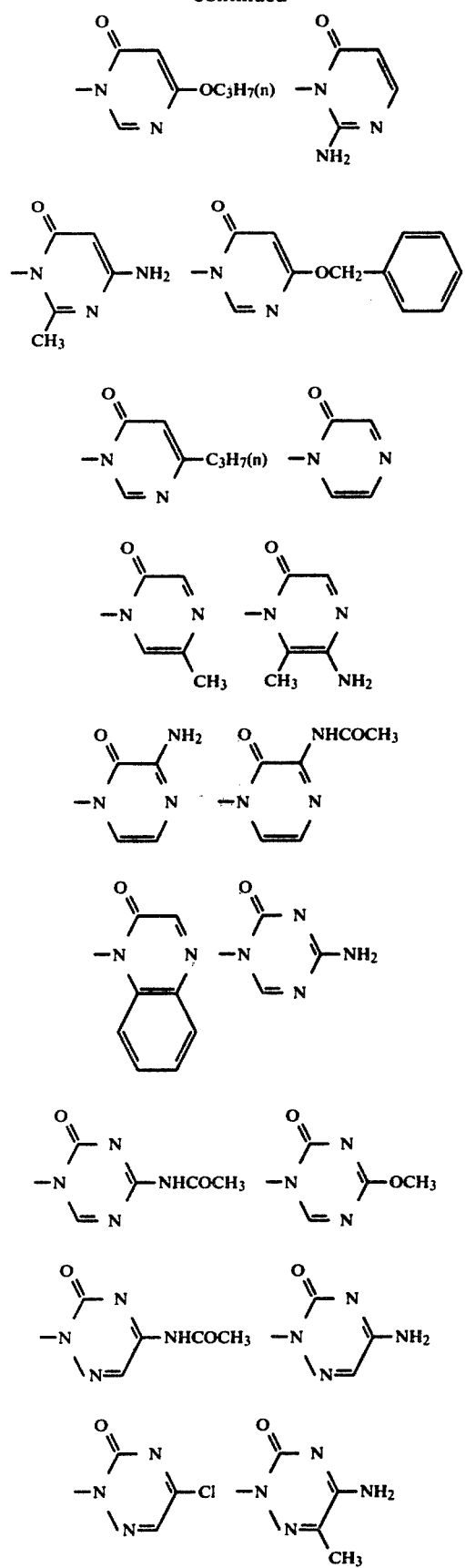
4
-continued
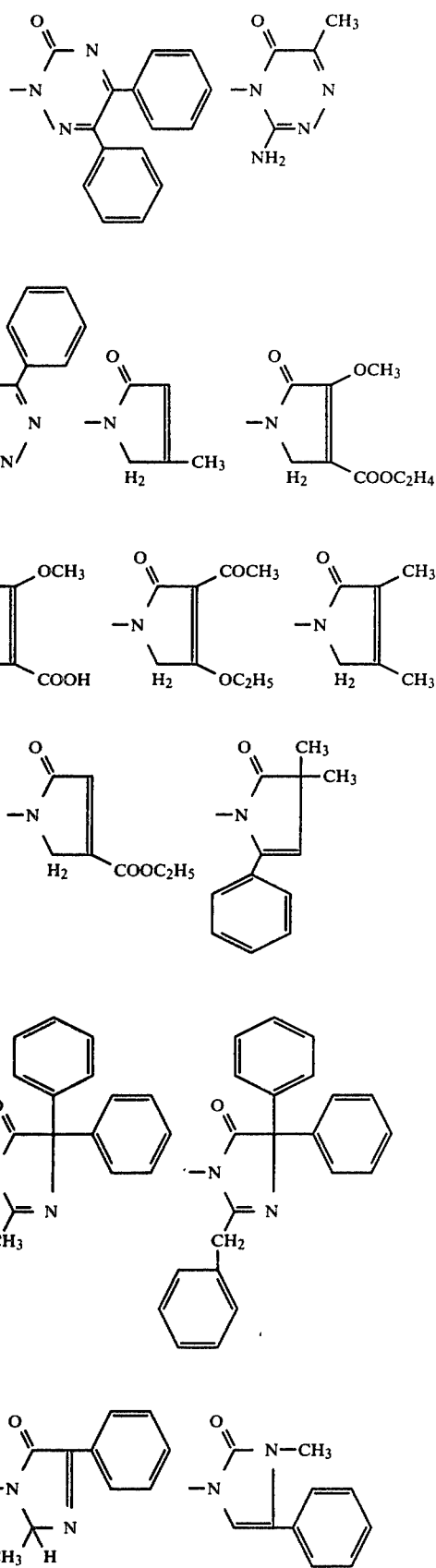

-continued

-continued

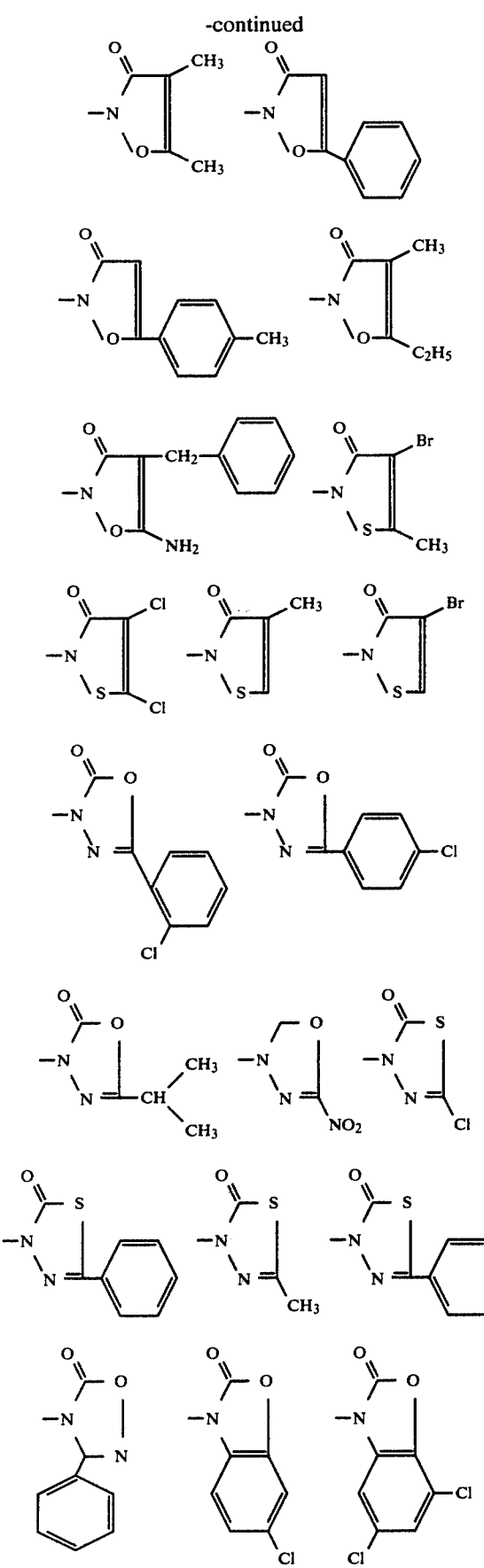

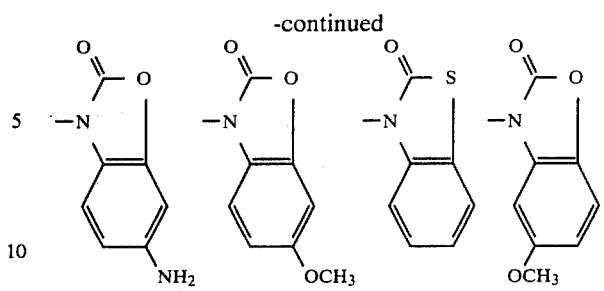

Yellow couplers capable of being substituted at their active points by such substituents as mentioned above may be any yellow couplers so far as they have active methylene groups in the molecules. When the said substituents are substituted in the active points of the yellow couplers, such excellent characteristics as mentioned previously are imparted to the couplers.

Typical concrete examples of the yellow couplers of the present invention are shown below, but yellow couplers according to the present invention are not limited to these.

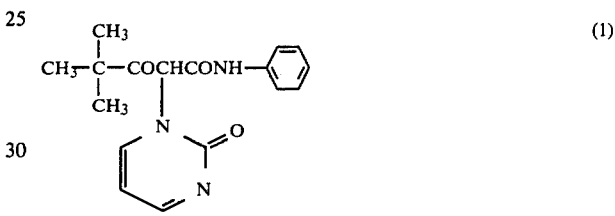

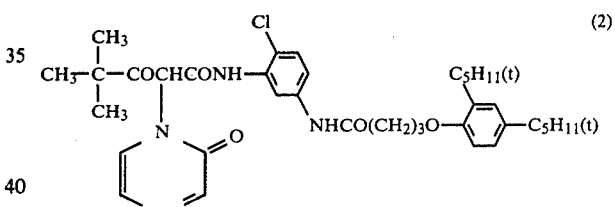

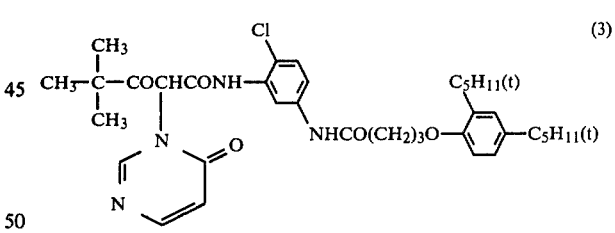

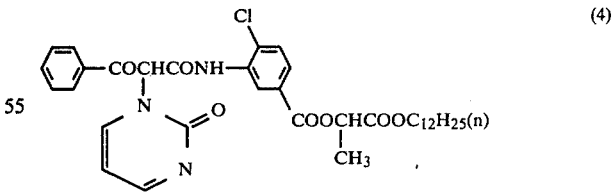

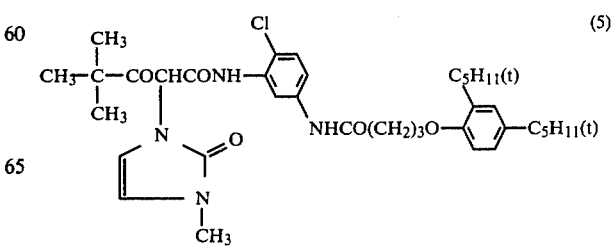

-continued
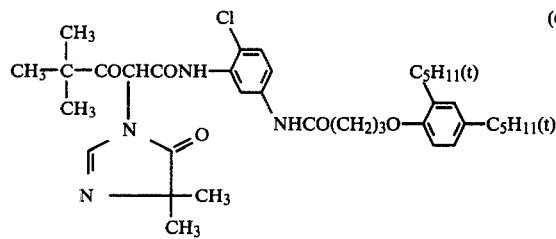 (6)
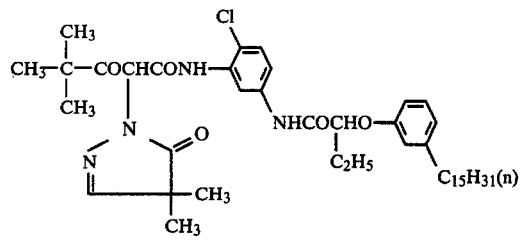 (7)
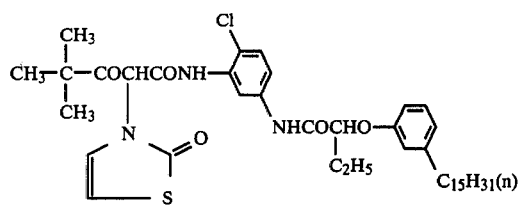 (8)
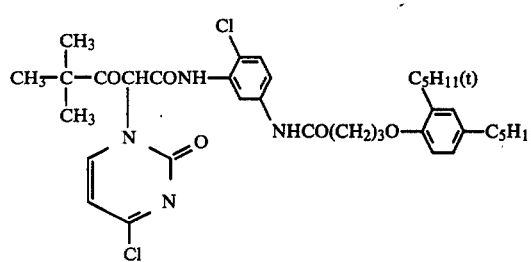 (9)
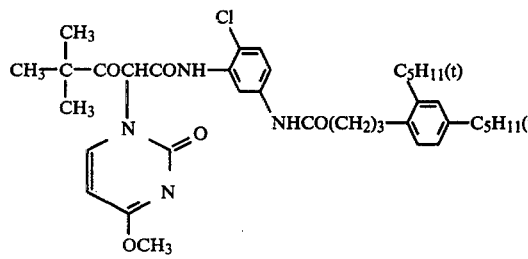 (10)
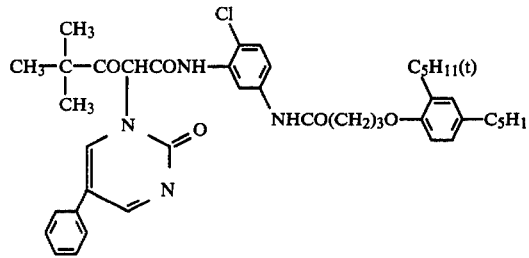 (11)
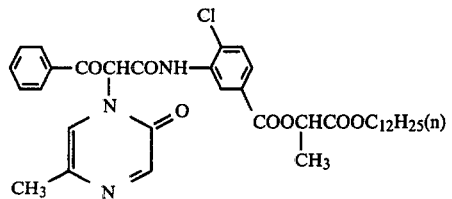 (12)
-continued
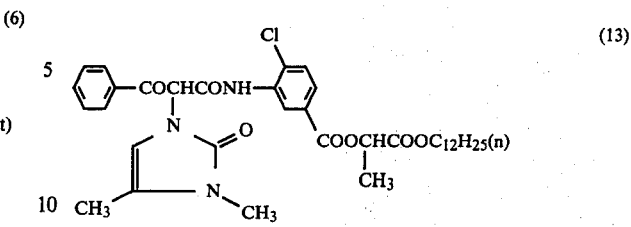 (13)
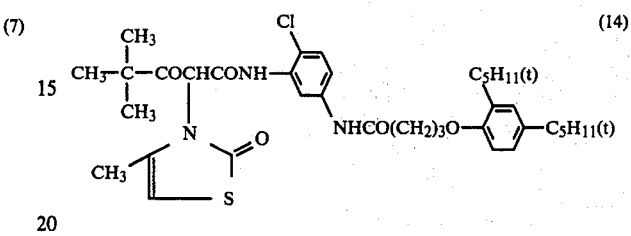 (14)
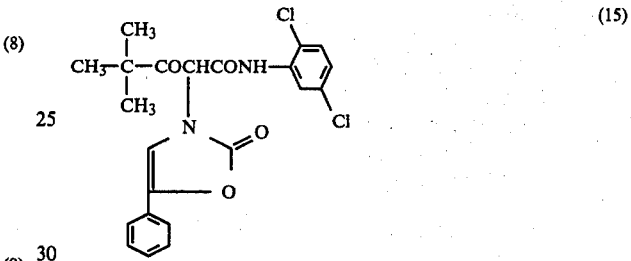 (15)
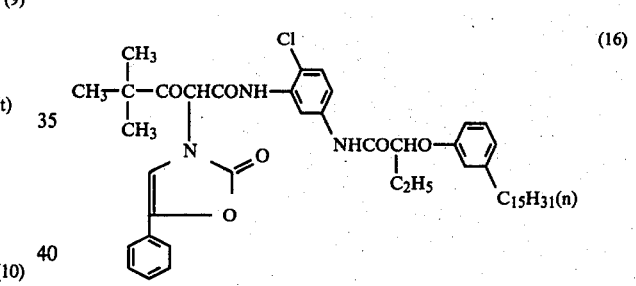 (16)
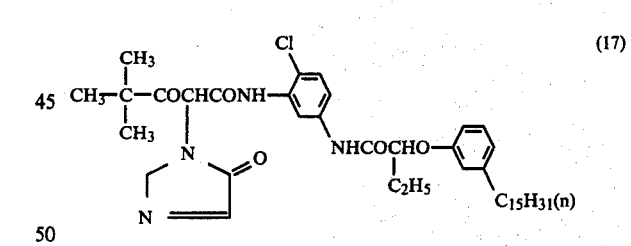 (17)
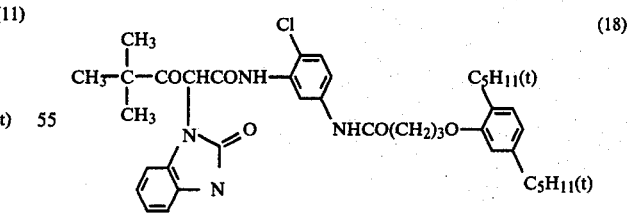 (18)
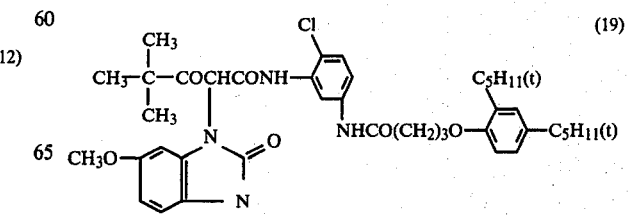 (19)

-continued
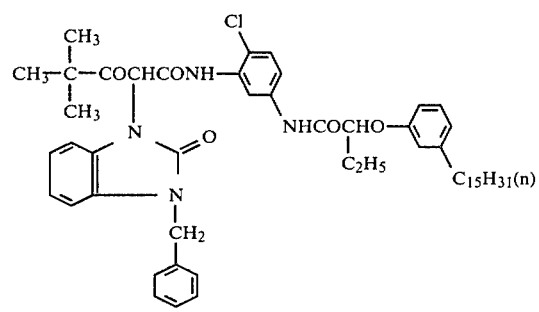 (20)
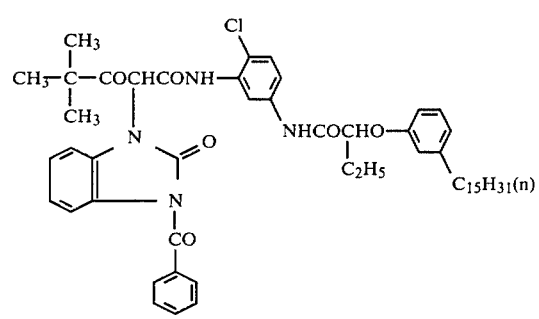 (21)
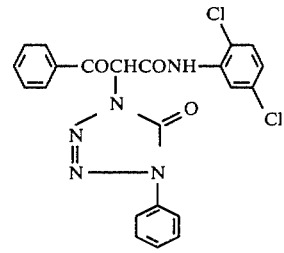 (22)
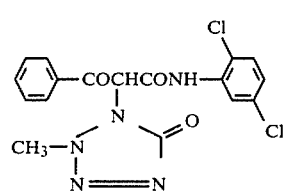 (23)
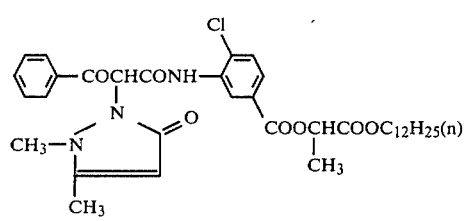 (24)
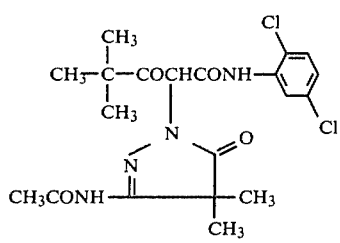 (25)
-continued
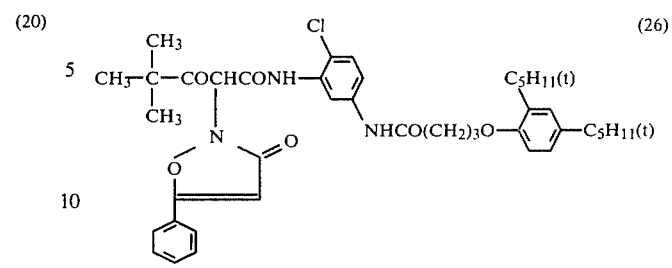 (26)
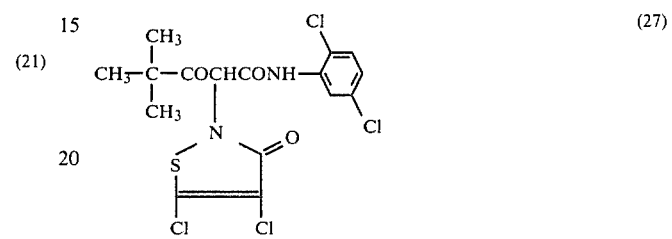 (27)
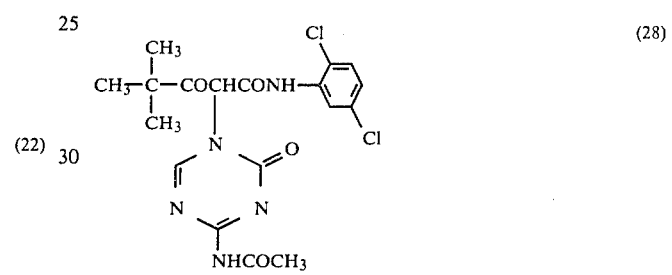 (28)
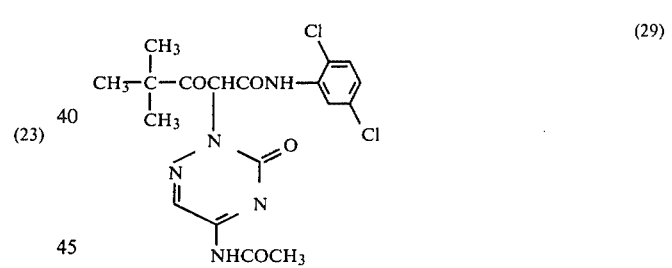 (29)
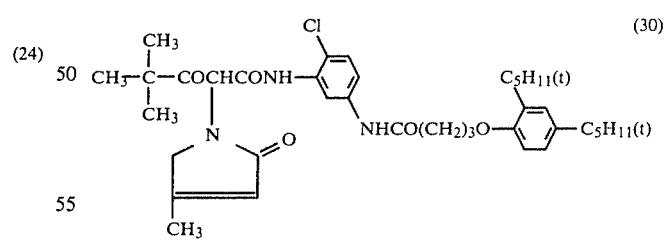 (30)
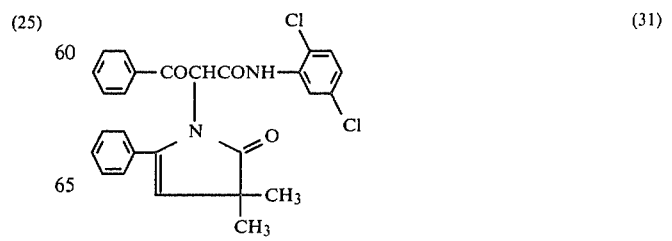 (31)

-continued
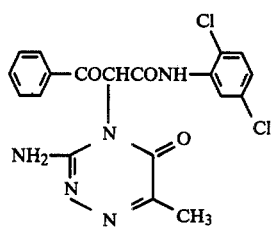 (32)
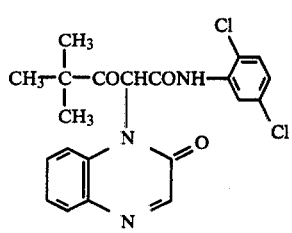 (33)
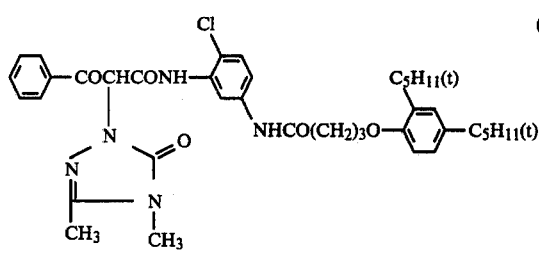 (34)
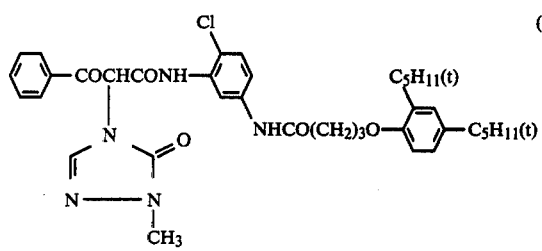 (35)
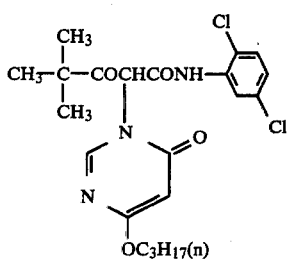 (36)
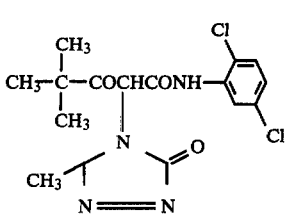 (37)
-continued
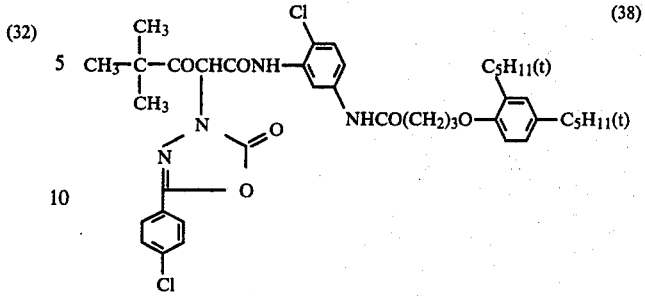 (38)
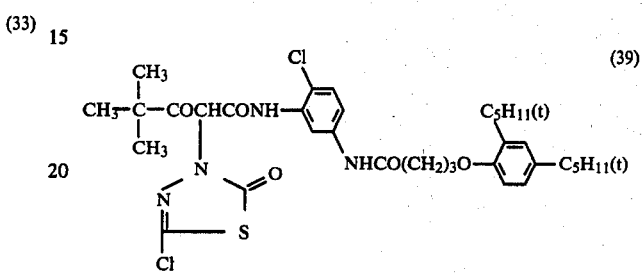 (39)
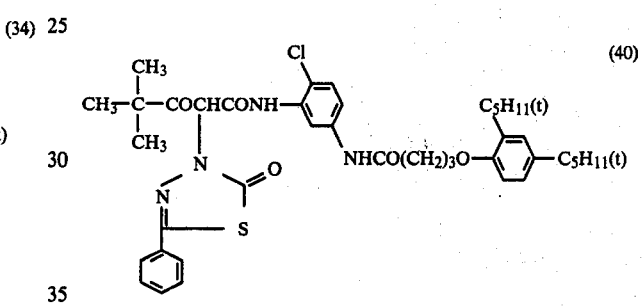 (40)
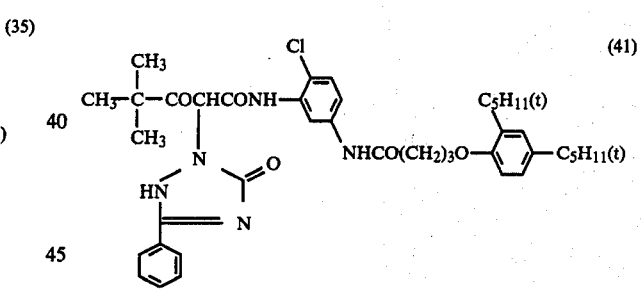 (41)
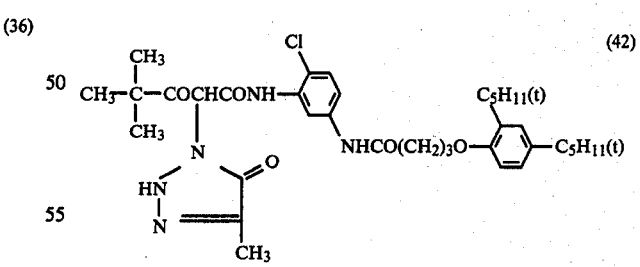 (42)
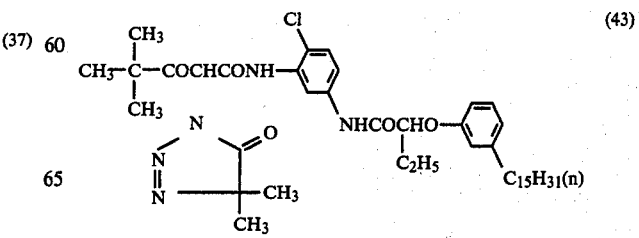 (43)

-continued

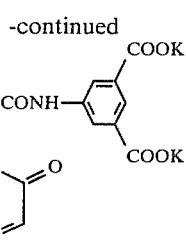
(44)

The above-mentioned yellow couplers of the present invention can be synthesized by reacting, for example, a yellow coupler having an active methylene group bonded to 2 carbonyl groups, in which coupler one of hydrogen atoms of the active methylene group has been substituted by a halogen atom, with a compound corresponding to such substituent, as pyrimidone or the like, having or not having such substituent as mentioned previously, in which a hydrogen atom has been bonded to the substituent.

Procedures for synthesizing typical couplers among the yellow couplers of the present invention are illustrated in detail below with reference to synthesis examples.

Synthesis Example 1

Synthesis of the coupler (1)

A mixture comprising 7.6 g. of α-pivalyl-α-chloroacetanilide, 3.2 g. of 2(1H)-pyrimidone and 3.3 g. of triethylamine was reacted under reflux for 3.5 hours in 40 ml. of acetonitrile. Thereafter, the reaction liquid was dried under reduced pressure, and the residue was recrystallized from ethyl alcohol to obtain white crystals, m.p. 201°-203° C.

| Elementary analysis (%): | | | |
|---|---|---|---|
| | C | H | N |
| Calculated | 65.16 | 6.11 | 13.41 |
| Found | 65.32 | 6.09 | 13.63 |

Synthesis Example 2

Synthesis of the coupler (2)

A mixture comprising 30.0 g. of α-pivalyl-α-chloro-5[γ-(2,4-di-t-amylphenoxy)-butylamide]-acetanilide, 5.3 g. of 2(1H)-pyrazolone and 5.5 g. of triethylamine was reacted under reflux for 6 hours in 150 ml. of acetonitrile. Thereafter, the reaction liquid was dried under reduced pressure, and the residue was recrystallized from n-hexane/ethyl alcohol to obtain white crystals, m.p. 182°-185° C.

| Elementary analysis (%): | | | |
|---|---|---|---|
| | C | H | N |
| Calculated | 66.80 | 7.42 | 8.42 |
| Found | 67.00 | 7.39 | 8.25 |

Synthesis Example 3

Synthesis of the coupler (6)

A mixture comprising 24.2 g. of α-pivalyl-α-chloro-2-chloro-5-[Y-(2,4-di-t-amylphenoxy)-butylamide]-acetanilide, 5.6 g. of 4,4-dimethyl-5-(1H)-imidazolone and 4.4 g. of triethylamine was reacted under reflux for 7 hours in 120 ml. of acetonitrile. Thereafter, the reaction liquid was dried under reduced pressure, and the residue was purified according to interfacial method using n-hexane/acetonitrile to obtain white crystals, m.p. 157°-159° C.

| Elementary analysis (%): | | | |
|---|---|---|---|
| | C | H | N |
| Calculated | 66.99 | 7.70 | 8.40 |
| Found | 66.76 | 7.66 | 8.24 |

Synthesis Example 4

Synthesis of the coupler (34)

A mixture comprising 29.4 g. of α-benzoyl-α-chloro-5-[γ-(2,4-di-t-amylphenoxy)-butylamide]-acetanilide, 6.2 g. of 3,4-dimethyl-$\Delta^2$-1,2,4-5(1H)-triazolone and 6.1 g. of triethylamine was reacted under reflux for 9 hours in 140 ml. of acetonitrile. Thereafter, the reaction liquid was dried under reduced pressure, and the residue was dissolved in methyl alcohol. Into the resulting solution, water was dropped with stirring to deposit crystals. The crystals were recovered by filtration, dried and then recrysallized from n-hexane/ethyl alcohol to obtain white crystals, m.p. 134°-136° C.

| Elementary analysis (%): | | | |
|---|---|---|---|
| | C | H | N |
| Calculated | 66.70 | 6.89 | 9.97 |
| Found | 66.68 | 6.91 | 9.99 |

Synthesis Example 5

Synthesis of the coupler (4)

A mixture comprising 17.8 g. of α-benzoyl-α-chloro-5-[α-(dodecylcarbonyl)-ethoxycarbonyl]-acetanilide, 2.8 g. of 2(1H)-pyrimidine and 3.3 g. of triethylamine was reacted under reflux for 7 hours in 100 ml. of acetonitrile. Thereafter, the reaction liquid was dried under reduced pressure, and the residue was recrystallized from ethyl alcohol to obtain white crystals, m.p. 171°-173° C.

| Elementary analysis (%): | | | |
|---|---|---|---|
| | C | H | N |
| Calculated | 64.45 | 6.49 | 6.44 |
| Found | 64.36 | 6.52 | 6.37 |

Synthesis Examples 6-10

Synthesis of the couplers (25), (27), (29), (33) and (36)

Synthesis Example 1 was repeated, except that the α-pivalyl-α-chloroacetanilide was replaced by 16.1 g. of α-pivalyl-α-chloro-2,5-dichloroacetanilide, and the 2(1H)-pyrimidone was replaced by each of the below-mentioned compounds, to obtain white crystals.

Coupler (25)—8.5 g. of 3-acetamide-4,4-dimethyl-2-pyrazolone (5)
Coupler (27)—9.4 g. of 4,5-dichloro-2-isothiazolone (5)
Coupler (29)—8.5 g. of 4-acetamide-as-triazolone (6)
Coupler (33)—8.0 g. of 2(1H)-quinaoxazolone
Coupler (36)—12.3 g. of 6-octyloxy-4(3H)-pyrimidone

| Coupler | m.p. (°C.) | Elementary analysis (%) | | | | | |
|---|---|---|---|---|---|---|---|
| | | Calculated | | | Found | | |
| | | C | H | N | C | H | N |
| (25) | 178–181 | 56.48 | 5.69 | 9.88 | 56.57 | 5.67 | 9.91 |
| (27) | 182–184 | 42.12 | 3.09 | 6.14 | 42.08 | 3.13 | 6.11 |
| (29) | 171–173 | 50.71 | 4.49 | 13.14 | 50.80 | 4.52 | 13.11 |
| (33) | 165–167 | 58.34 | 4.43 | 9.72 | 58.27 | 4.42 | 9.67 |
| (36) | 152–154 | 66.70 | 6.89 | 9.97 | 66.42 | 6.85 | 9.99 |

Synthesis Examples 11–16

Synthesis of the Couplers (11), (18), (26), (30), (38) and (41)

Synthesis Example 2 was repeated except that the 2(1H)-pyrazolone was replaced by each of the below-mentioned compounds, to obtain white crystals.
Coupler (11)—9.5 g. of 5-phenyl-2(1H)-pyrimidone
Coupler (18)—7.4 g. of 2-benzoxazolone
Coupler (26)—8.9 g. of 4-isoxazolone (5)
Coupler (30)—5.3 g. of 4-methyl-3-prolone (2)
Coupler (38)—10.8 g. of 5-phenyl-$\Delta^4$-1,3,4-oxadiazolone (5)
Coupler (41)—8.9 g of 3-phenyl-$\Delta^3$-1,2,4-triazolone (5)

| Coupler | m.p. (°C.) | Elementary analysis (%) | | | | | |
|---|---|---|---|---|---|---|---|
| | | Calculated | | | Found | | |
| | | C | H | N | C | H | N |
| (11) | 151–154 | 69.66 | 7.21 | 7.56 | 69.73 | 7.19 | 7.59 |
| (18) | 146–149 | 68.11 | 7.29 | 5.96 | 68.20 | 7.31 | 5.99 |
| (26) | 133–135 | 68.97 | 7.30 | 5.75 | 69.00 | 7.29 | 5.77 |
| (30) | 125–127 | 68.39 | 8.01 | 6.30 | 68.35 | 8.03 | 6.32 |
| (38) | 150–152 | 64.22 | 6.70 | 7.31 | 64.17 | 6.69 | 7.27 |
| (41) | 120–122 | 67.42 | 7.18 | 9.59 | 67.50 | 7.20 | 9.55 |

Synthesis Examples 17–19

Synthesis of the couplers (12), (13) and (24)

Synthesis Example 5 was repeated, except that the 2(1H)-pyrimidone was replaced by each of the below-mentioned compounds, to obtain white crystals.
Coupler (12)—3.6 g. of 5-methyl-2(1H)-pyrazone
Coupler (13)—3.7 g. of 3,4-dimethyl-4-imidazolone (2)
Coupler (24)—3.7 g. of 2,3-dimethyl-3-pyrazolone

| Coupler | m.p. (°C.) | Elementary analysis (%) | | | | | |
|---|---|---|---|---|---|---|---|
| | | Calculated | | | Found | | |
| | | C | H | N | C | H | N |
| (12) | 131–133 | 69.90 | 6.66 | 6.31 | 65.09 | 6.57 | 6.42 |
| (13) | 141–144 | 64.70 | 6.94 | 6.29 | 64.71 | 6.93 | 6.31 |
| (24) | 127–130 | 64.61 | 7.08 | 6.28 | 64.54 | 7.10 | 6.23 |

The thus obtained yellow couplers of the present invention are useful as so-called protect dispersion type couplers which are used in the form of solutions in sparingly water-miscible high boiling organic solvents having boiling points of more than 175° C. such as, for example, dibutyl phthalate and tricresyl phosphate. Alternatively, they may be used in the form of solutions in substantially water-insoluble low boiling organic solvents such as ethyl acetate and butyl acetate, or in water-soluble low boiling organic solvents such as methanol, ethanol and methylisobutylketone, without using the above-mentioned high boiling organic solvents. Some of the couplers of the present invention are extremely useful as so-called Fischer dispersion type couplers which are used in the form of dispersions in alkaline methanol or aqueous solutions.

Furthermore, the yellow couplers of the present invention are useful also as so-called external type couplers used in a method in which a coupler is incorporated into a developer to form a dye image, and as couplers for use in so-called diffusion transfer method in which a photosensitive layer and an image-receiving sheet are contacted during development to form a transfer image on the image-receiving sheet.

Thus, the yellow couplers of the present invention can form yellow dye images according to various methods, and the dyes formed from the yellow couplers of the present invention have excellent spectral absorption characteristics and are extremely stable to light, heat, humidity and pressure. In case the yellow couplers of the present invention are incorporated into color photographic materials, the photosensitive layers can be made thinner, with the result that the photographic materials are enhanced in sharpness or improved in developability. Even when the development time is prolonged, the photographic materials are scarcely increased in fog and form no such color stains as seen in the case where conventional couplers are used.

Color developing agents, which are used in combination with the yellow couplers of the present invention, include phenylenediamine type developing agents such as diethyl-p-phenylenediamine hydrochloride, monomethyl-p-phenylenediamine hydrochloride, dimethyl-p-phenylenediamine hydrochoride, 2-amino-5-diethylaminotoluene hydrochloride, 2-amino-5-(N-ethyl-N-dodecylamino)-toluene, N-ethyl-N-$\beta$-methanesulfonamidoethyl-3-methyl-4-aminoaniline sulfate, N-ethyl-N-$\beta$-methanesulfonamidoethyl-4-aminoaniline and 4-N-ethyl-N-$\beta$-hydroxyethyl-aminoaniline, and p-aminophenol type developing agents in which the amino groups have not been substituted. Some of the yellow couplers of the present invention are used as external type couplers in alkaline developers, as mentioned previously. Even if the said developers contain sulfites, carbonates, bisulfites, bromides or iodides of alkali metals, the yellow couplers of the present invention do not cause any detrimental interactions with said compounds.

A typical example of such developers is as follows:

| | |
|---|---|
| 2-Amino-5-diethylaminotoluene hydrochloride | 2.0 g. |
| Anhydrous sodium sulfite | 2.0 g. |
| Anhydrous sodium carbonate | 2.0 g. |
| Potassium bromide | 1.0 g. |
| Yellow coupler (1) | 2.0 g. |
| Water to make | 1,000 ml. |

The yellow couplers of the present invention are applicable to various color photographic materials which are susceptible to such electromagnetic wave energies as, for example, ultraviolet rays, visible rays, infrared rays, X-rays, $\gamma$-rays and microwaves.

For incorporation of the yellow couplers of the present invention into color photographic emulsions, any known procedure may be adopted. For example, in order to use the couplers as the previously mentioned protect type couplers, there may be employed such procedure as mentioned below.

One or more of the couplers are dissolved in one or more high boiling organic solvents having boiling points of more than 175° C. such as tricresyl phosphate and dibutyl phthalate, and low boiling organic solvents such as ethyl acetate and butyl propionate. The resulting solution is mixed with an aqueous gelatin solution containing a surfactant, and then dispersed by means of a high speed rotary mixer or colloid mill. Subsequently, the resulting dispersion is incorporated directly into a silver halide photographic emulsion, which is then coated on a support. Alternatively, the said dispersion may be set, finely cut, freed from the low boiling solvent by water-washing or the like means, and thereafter incorporated into a silver halide photographic emulsion, which is then coated on a support. The amount of the coupler used in the above is preferably 10 to 300 g. per mole of silver halide, in general, but is, of course, variable depending on the application purpose.

Among the yellow couplers of the present invention, the couplers (6), (8), (12), (17), (20) and (34), for example, may be dispersed in the emulsion in the same manner as above, without using any high boiling organic solvents, and the coupler (44), for example, may be dispersed in the emulsion according to the Fischer dispersion method. Further, the couplers (1), (15), (23), (28), (29) and (32) may be incorporated into developers.

Photographic emulsions used to form yellow images by use of the yellow couplers of the present invention may contain various silver halides such as silver chloride, silver iodobromide, silver chlorobromide, etc. Further, the emulsions may have been chemically sensitized or optically sensitized by use of carbocyanine dyes or merocyanine dyes, and may have been incorporated with ordinary photographic additives such as antifoggants, stabilizers, anti-stain agents, anti-irradiation agents, physical property-improving high molecular additives, coating aids, etc.

When color photographic materials incorporated with the yellow couplers of the present invention are additionally incorporated with ultraviolet absorbers, the resulting yellow images can be further enhanced in fastness.

Color developers for developing color photographic materials incorporated with the yellow couplers of the present invention, or external color developers incorporated with the yellow couplers of the present invention, may contain development-controlling agents, e.g. citrazinic acid, in addition to the aforesaid developing agents.

Figure 2:
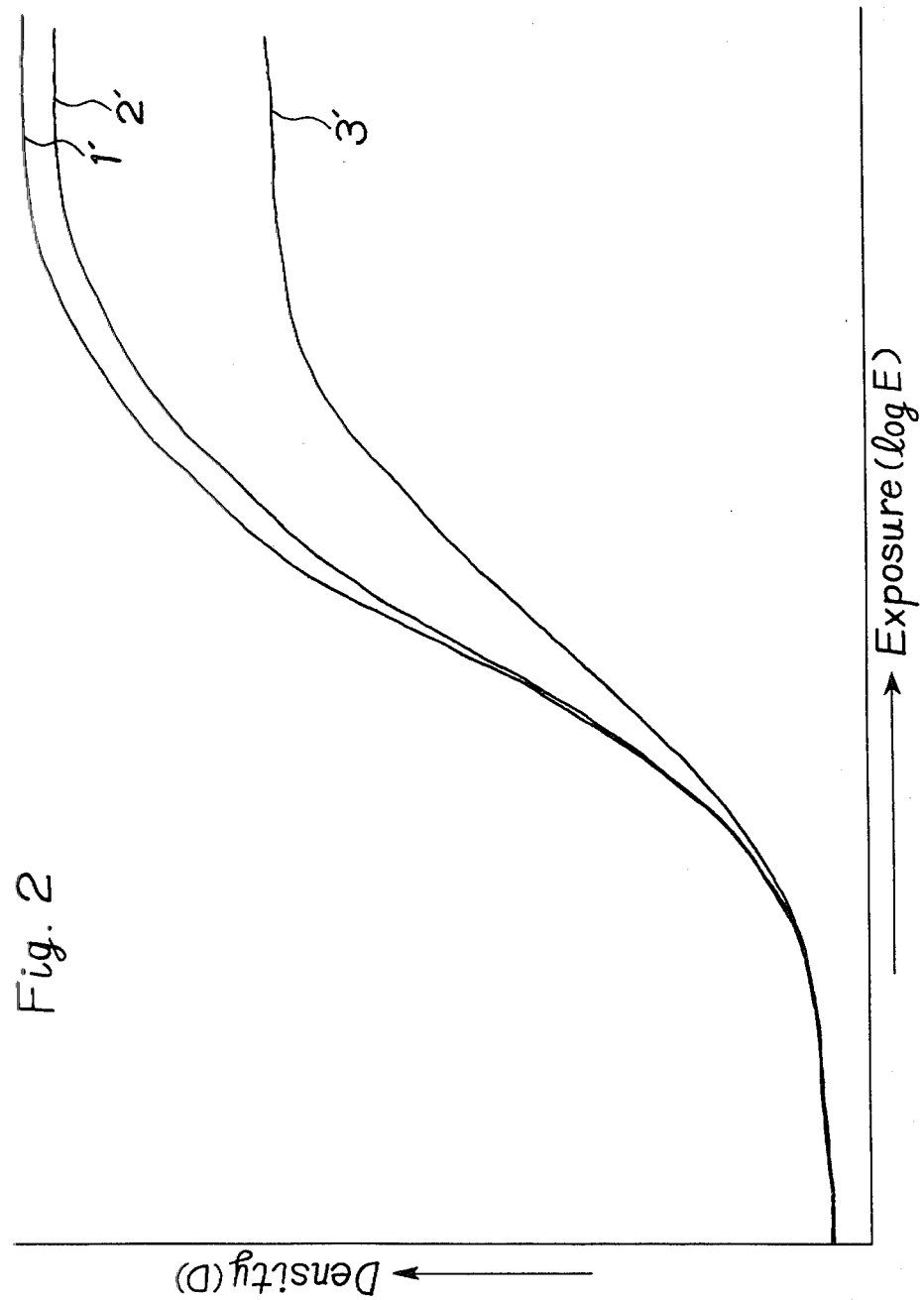

FIGS. 1 and 2 show characteristic curves representing the yellow dye densities to blue light of the samples obtained in Example 2. In FIGS. 1 and 2, the curves 1, 2, 1' and 2' show the case where the couplers of the present invention were used, and the curves 3, 4 and 3' show the case where the control samples were used.

The present invention is illustrated in detail below with reference to examples, but the scope of the invention is not limited to the examples.

EXAMPLE 1

20.0 Grams of each of the couplers (2), (4), (8), (13), (17), (19), (20), (21), (26), (40), (41) and (43) was completely dissolved at 60° C. in a mixed liquid comprising 20 ml. of dibutyl phthalate and 60 ml. of ethyl acetate. The resulting solution was mixed with 10 ml. of a 6% aqueous solution of Alkanol B (alkylnaphthalene sulfonate, produced by Du Pont Co.) and 200 ml. of a 6% aqueous gelatin solution, and then dispersed by means of a colloid mill to prepare a coupler dispersion. This dispersion was added to 1 kg. of a high speed silver iodobromide emulsion, which was then coated on a film base and subsequently dried to obtain a photographic material having a stable coating film. This photographic material was exposed according to an ordinary procedure, developed at 20° C. for 10 minutes with a developer of the below-mentioned composition, and then subjected to ordinary stopping, fixing and bleaching to prepare samples. Developer composition:

| | |
|---|---|
| N-Ethyl-N-$\beta$-methanesulfonamidoethyl-3-methyl-4-aminoaniline hydrochloride | 5.0 g. |
| Anhydrous sodium sulfite | 2.0 g. |
| Benzyl alcohol | 3.8 g. |
| Sodium carbonate (monohydrate) | 50.0 g. |
| Potassium bromide | 1.0 g. |
| Sodium hydroxide | 0.55 g. |
| Water to make | 1,000 ml. |

Separately, control samples were prepared in the same manner as above, except that the coupler was replaced by each of an unsubstituted type coupler [Control coupler (1)], which was identical in matrix structure with the couplers (2), (19), (26), (40) and (41), an unsubstituted type coupler [Control coupler (2)], which was identical in matrix structure with the couplers (4) and (13), an an unsubstituted type coupler [Control coupler (3)], which was identical in matrix structure with the couplers (8), (17), (20), (21) and (43).

The samples and control samples were individually measured in absorption maximum ($\lambda_{max}$) and density maximum ($D_{max}$) of yellow image and in fastness of yellow image. The results obtained were as set forth in Table 1.

TABLE 1

| Sample No. | Coupler | | $\lambda_{max}$ | $D_{max}$ | Yellow image Residual ration (%) | |
|---|---|---|---|---|---|---|
| | | | | | Light fastness | Humidity fastness |
| 1 | Control coupler | (1) | 448 | 1.23 | 98 | 99 |
| 2 | Coupler | (2) | 448 | 2.11 | 99 | 99 |
| 3 | " | (19) | 448 | 2.21 | 99 | 99 |
| 4 | " | (26) | 448 | 2.35 | 98 | 99 |
| 5 | " | (40) | 448 | 2.19 | 98 | 100 |
| 6 | " | (41) | 448 | 2.37 | 98 | 100 |
| 7 | Control coupler | (2) | 453 | 2.10 | 85 | 93 |
| 8 | Coupler | (4) | 453 | 2.79 | 85 | 93 |
| 9 | " | (13) | 453 | 2.99 | 85 | 93 |
| 10 | Control coupler | (3) | 448 | 1.41 | 99 | 99 |
| 11 | Coupler | (9) | 448 | 2.31 | 99 | 99 |
| 12 | " | (17) | 448 | 2.27 | 99 | 99 |
| 13 | " | (20) | 448 | 2.45 | 100 | 100 |
| 14 | " | (21) | 448 | 2.49 | 100 | 99 |
| 15 | " | (43) | 448 | 2.38 | 99 | 99 |

$\lambda_{max}$: Spectral absorption maximum wavelength (m$\mu$)
$D_{max}$: Density maxiumum
Residual ratio: Ratio (%) of dye left after treating a portion of each sample with initial density 1.0 under the following conditions:
Light fastness: Irradiation with a Xenon arc lamp at 50° C. for 30 hours.
Humidity fastness: Incubation at 50° C. and RH 80% for 7 days.

As is clear from Table 1, it is understood that the yellow couplers of the present invention show excellent characteristics and are extremely useful as yellow couplers for use in multi-layered multicolor photographic materials.

EXAMPLE 2

Using the couplers (7), (9), (12) and (24) and the same control couplers (1), (2) and (3) as in Example 1, samples and control samples were prepared in the same manner as in Example 1. These samples were individually measured, by means of densitometer, in density of yellow dye to blue light at each stage. The results obtained were as shown in FIGS. 1 and 2, in which the horizontal axis represents the exposure amount (log E) and the vertical axis the density (D).

In FIG. 1, the curve 1 shows the case where the coupler (7) was used, the curve 2 the coupler (9), the curve 3 the control coupler (3) identical in matrix with the coupler (7), and the curve 4 the control coupler (1) identical in matrix structure with the coupler (9), and in FIG. 2, the curve 1' shows the case where the coupler (12) was used, the curve 2' the coupler (24), and the curve 3' the control coupler (2) identical in matrix structure with the couplers (12) and (24).

As is clear from FIGS. 1 and 2, it is understood that the yellow couplers of the present invention are successfully usable even if the amount of silver used is one-half the conventional amount.

EXAMPLE 3

The coupler (44) was dispersed in a mixed solution comprising ethanol and water, and then dissolved in a 10% aqueous sodium hydroxide solution. The resulting solution was mixed with a gelatin solution (containing 12% of gelatin and 5.13% of Alkanol B), and then neutralized with acetic acid. The mixed solution was subsequently dispersed in a silver iodobromide solution, which was then coated on a support and dried to obtain a photographic material. The photographic material was exposed according to an ordinary procedure, developed at 20° C. for 10 minutes with the same developer as in Example 1, and then subjected to 3 bath-treatment of bleach-fixing, water-washing and stabilization to prepare a sample.

Separately, a control sample was prepared in the same manner as above, except that the coupler was replaced by an unsubstituted type coupler [Control coupler (4)] which was identical in matrix structure with the coupler (44).

The thus prepared sample and control sample were individually measured in fog, $\lambda_{max}$ and $D_{max}$. The results obtained were as set forth in Table 2.

TABLE 2

| Coupler | Fog | $\lambda_{max}$ | $D_{max}$ |
| --- | --- | --- | --- |
| Coupler (44) | 0.13 | 450 | 2.61 |
| Control coupler (4) | 0.17 | 450 | 1.89 |

As is clear from Table 2, it is understood that even when Fischer dispersion method is employed, the yellow coupler of the present invention provides excellent photographic properties.

EXAMPLE 4

Commerically available silver iodobromide color photographic materials were individually exposed and then developed with the below-mentioned developer incorporated with each of the couplers (1), (15) and (27), an unsubstituted type coupler [Control coupler (5)] identical in matrix structure with the coupler (1), and an unsubstituted type coupler [Control coupler (6)] identical in matrix structure with the couplers (15) and (27), to prepare samples. Developer composition:

| 2-Amino-5-diethylaminotoluene hydrochloride | 2.0 g. |
| --- | --- |

-continued

| Anhydrous sodium sulfite | 2.0 g. |
| --- | --- |
| Anhydrous sodium carbonate | 20.0 g. |
| Potassium bromide | 1.0 g. |
| Coupler | 2.0 g. |
| Water to make | 1,000 ml. |

The samples were measured in fog, $\lambda_{max}$ and $D_{max}$ to obtain the results shown in Table 3.

TABLE 3

| Coupler (1) | Fog | $\lambda_{mzx}$ | $D_{max}$ |
| --- | --- | --- | --- |
| Coupler (1) | 0.05 | 443 | 2.11 |
| Control coupler (5) | 0.05 | 443 | 1.27 |
| Coupler (15) | 0.04 | 450 | 2.23 |
| Coupler (27) | 0.04 | 450 | 2.31 |
| Control coupler (6) | 0.04 | 450 | 1.26 |

As is clear from Table 3, it is understood that the couplers of the present invention are quite useful also as external couplers.

What we claim is:

1. A process for forming a yellow color image which comprises contacting exposed silver halide grains with a developer for said silver halide grains in the presence of a yellow coupler of the formula,

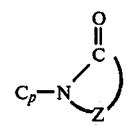

wherein $C_p$ is a residue formed by removing one hydrogen atom of the active methylene group of a yellow coupler having an active methylene group; and

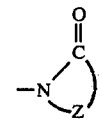

is selected from the group consisting of

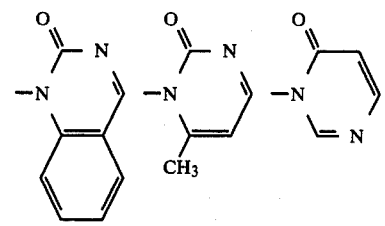

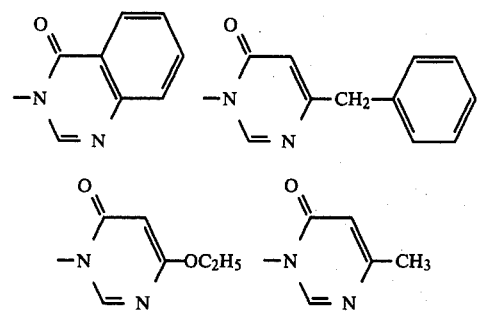

-continued
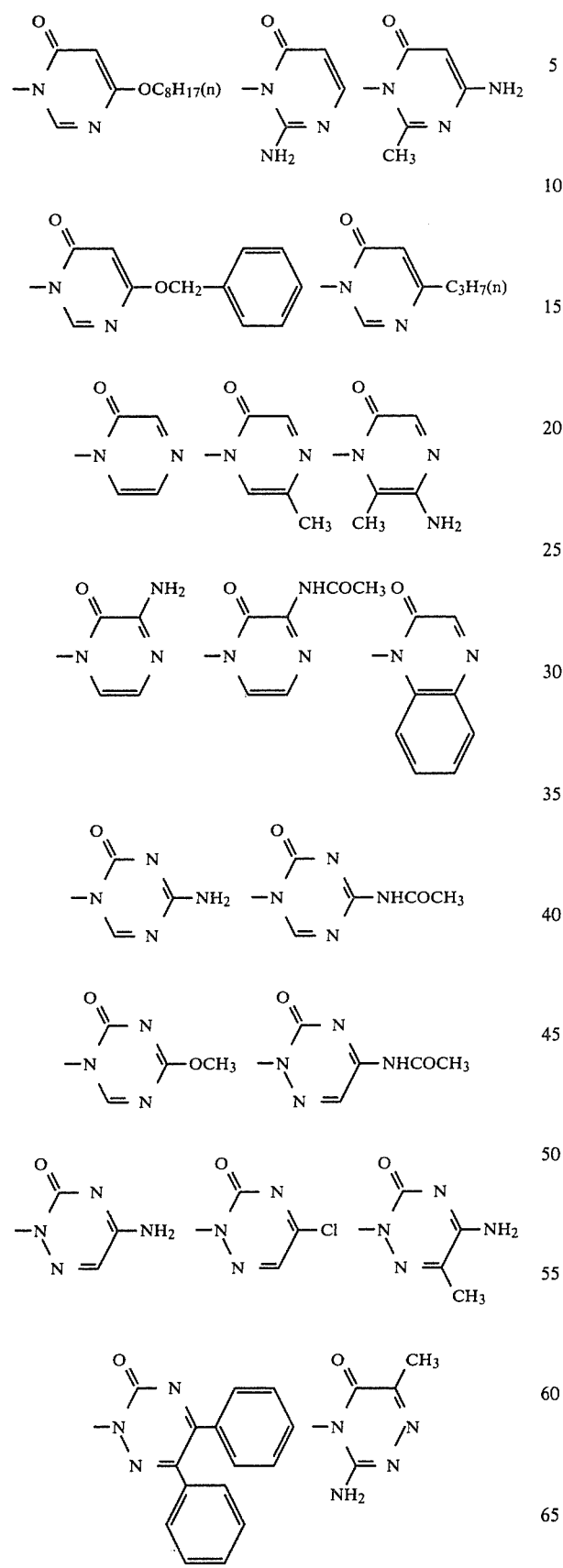
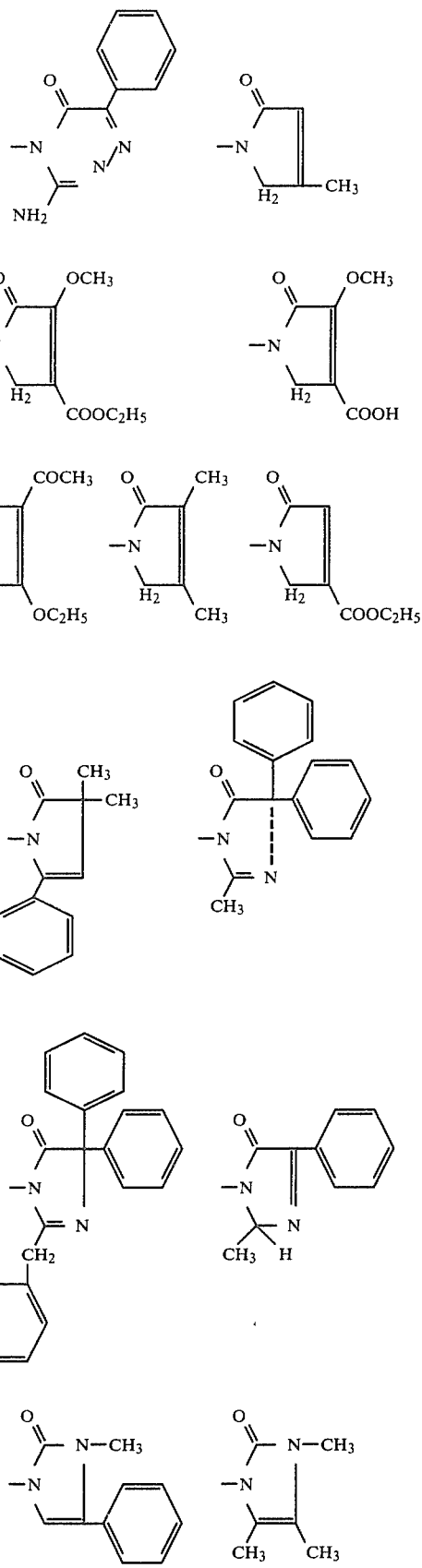

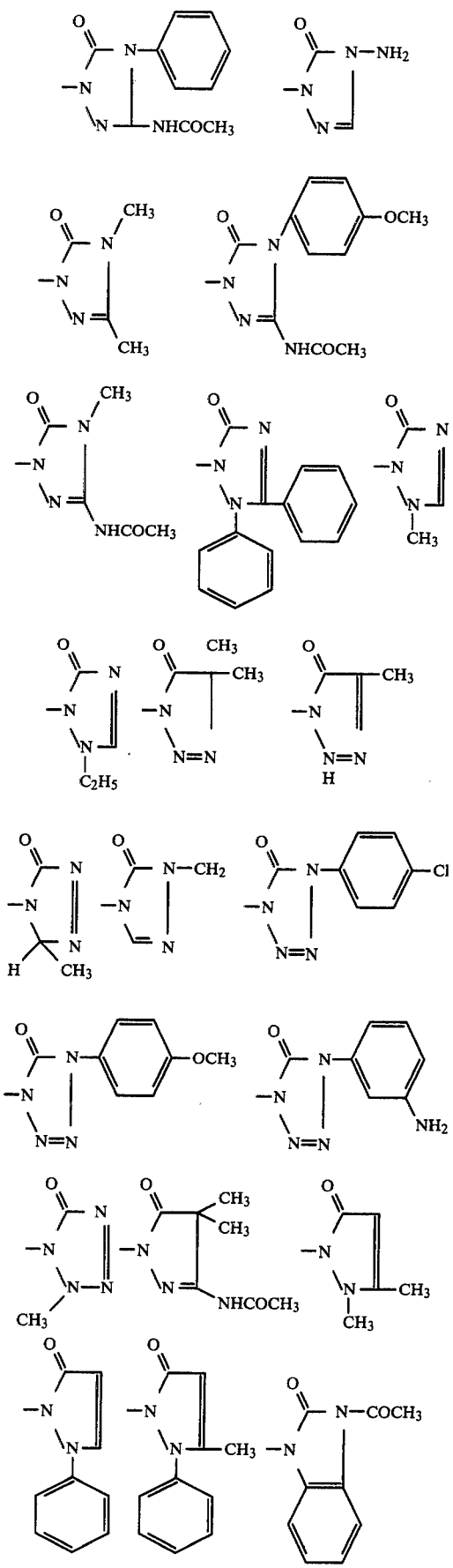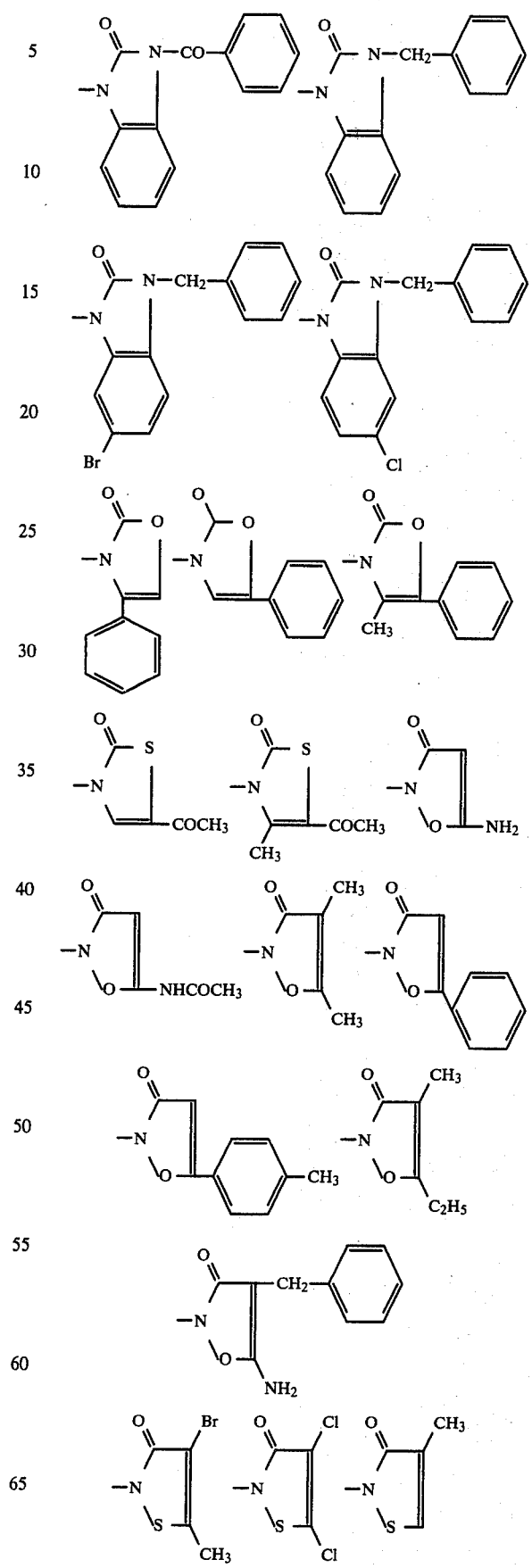

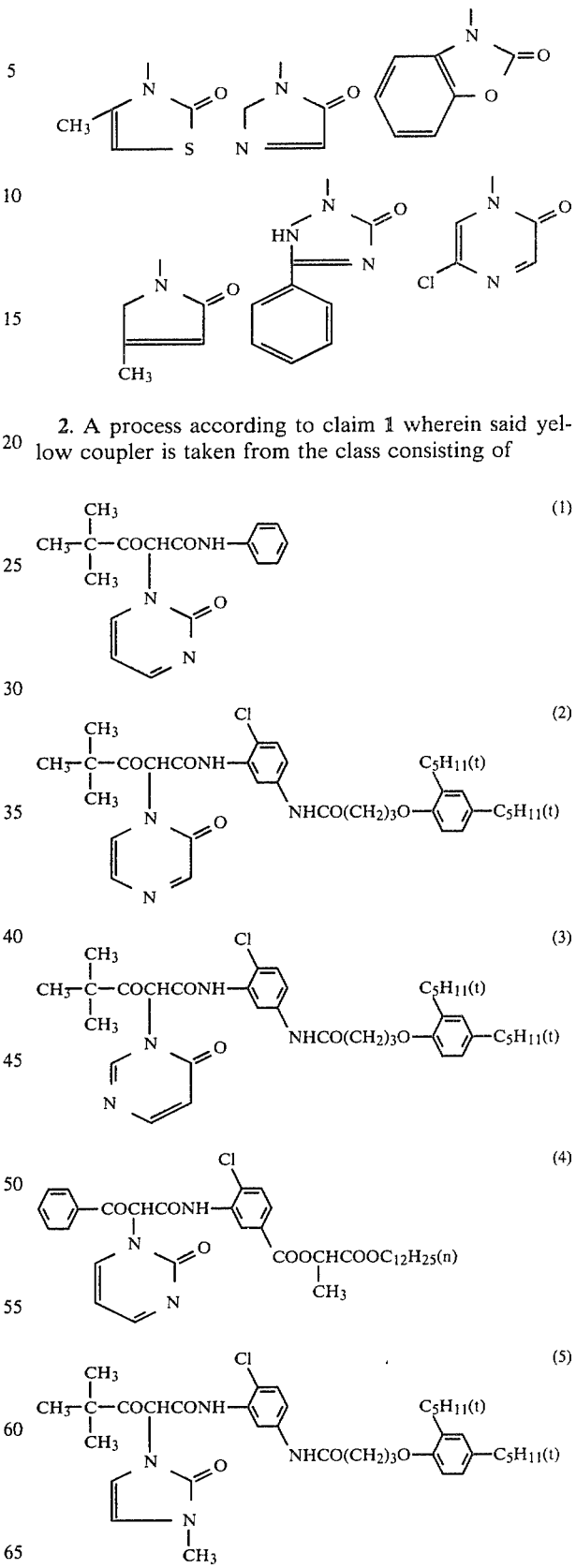
2. A process according to claim 1 wherein said yellow coupler is taken from the class consisting of -continued
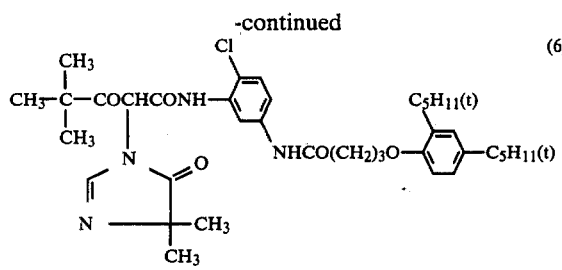 (6)
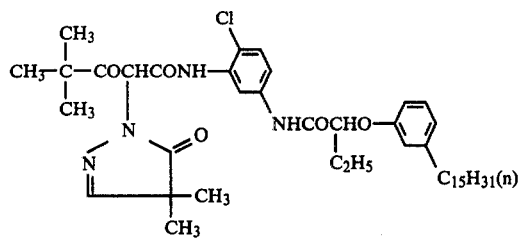 (7)
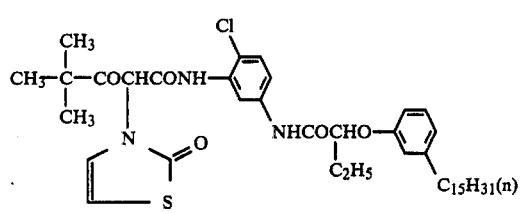 (8)
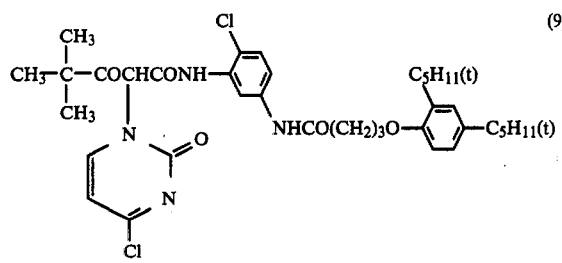 (9)
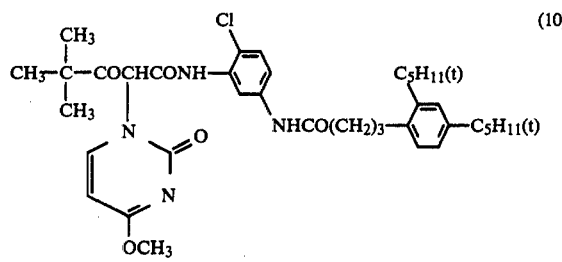 (10)
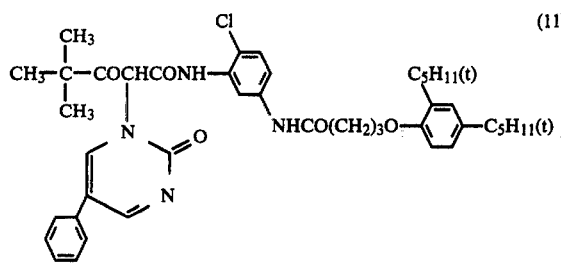 (11)
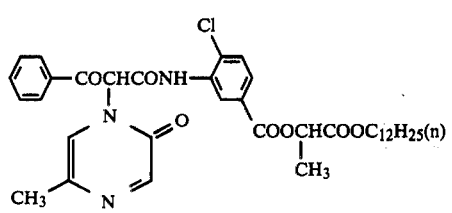 (12)
-continued
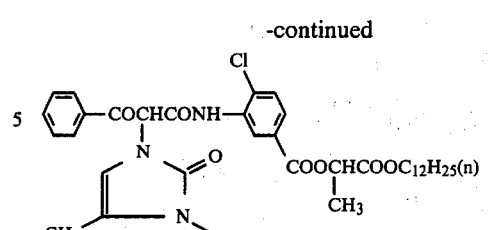 (13)
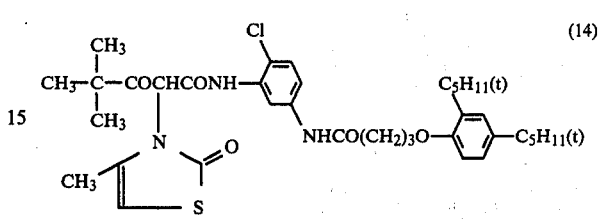 (14)
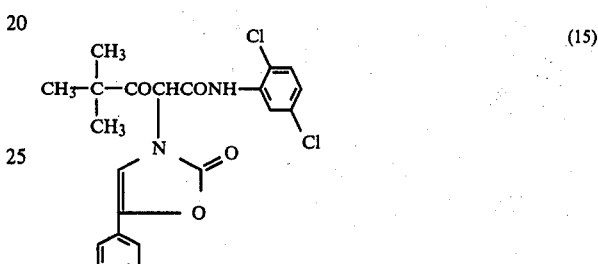 (15)
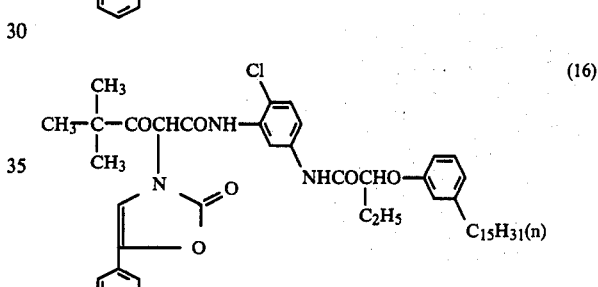 (16)
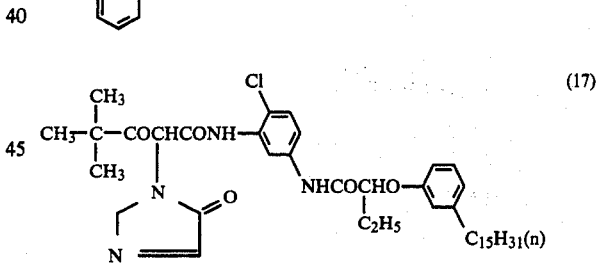 (17)
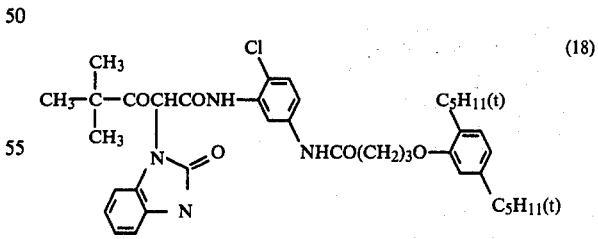 (18)
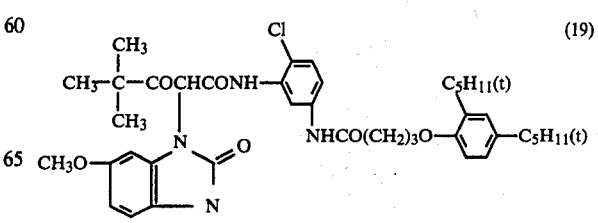 (19)

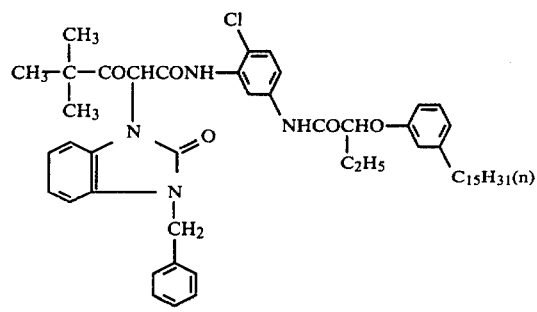
(20)
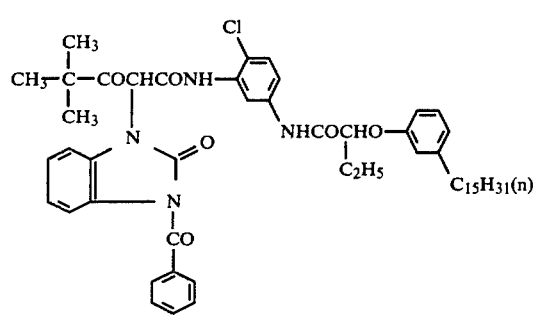
(21)
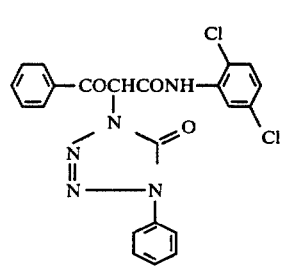
(22)
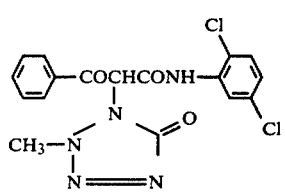
(23)
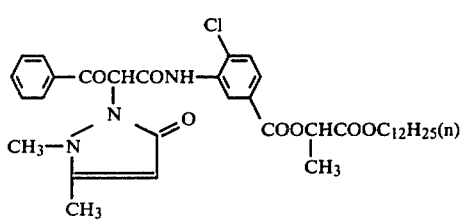
(24)
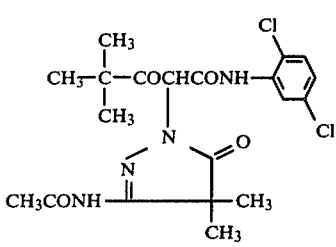
(25)
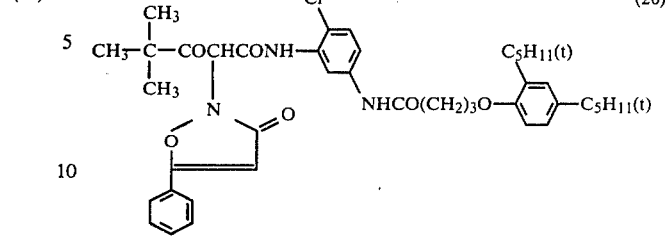
(26)
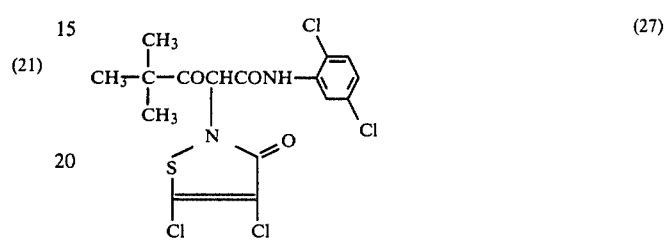
(27)
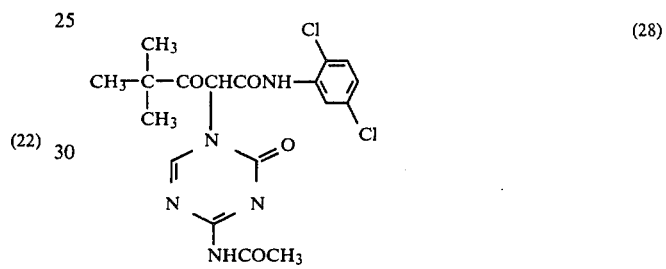
(28)
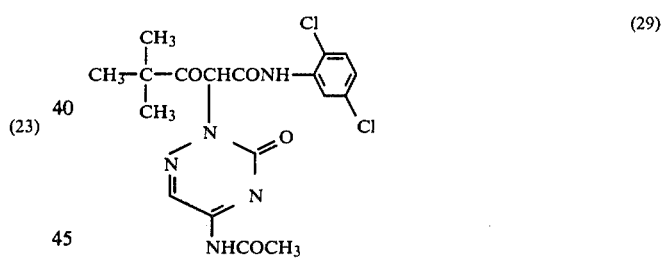
(29)
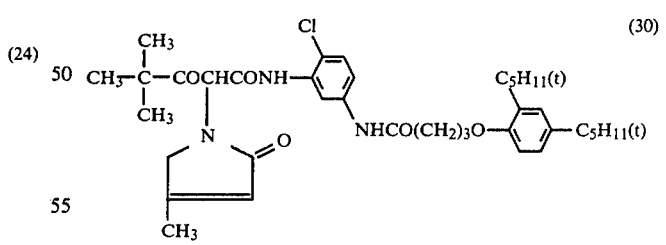
(30)
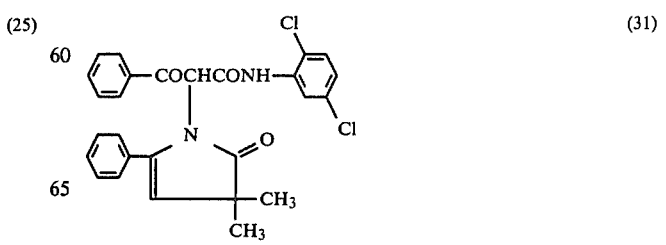
(31)

-continued
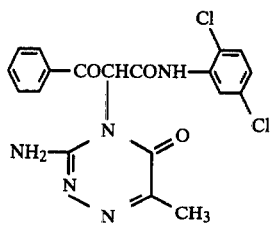 (32)
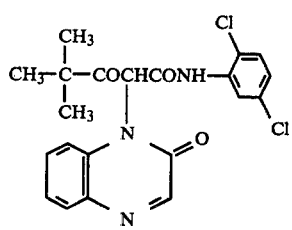 (33)
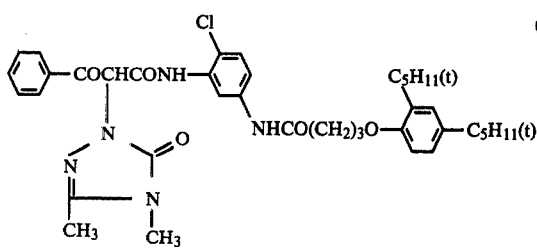 (34)
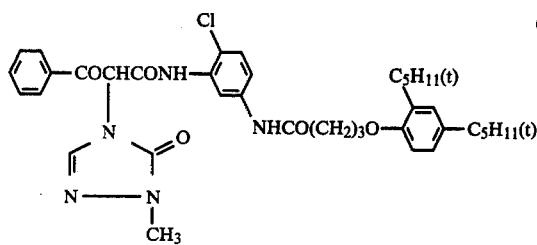 (35)
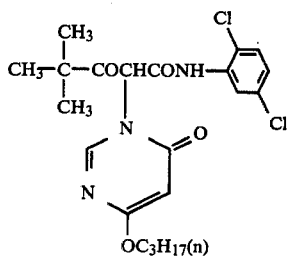 (36)
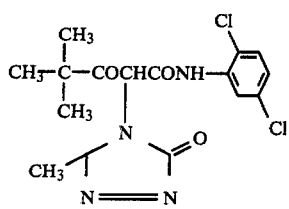 (37)
-continued
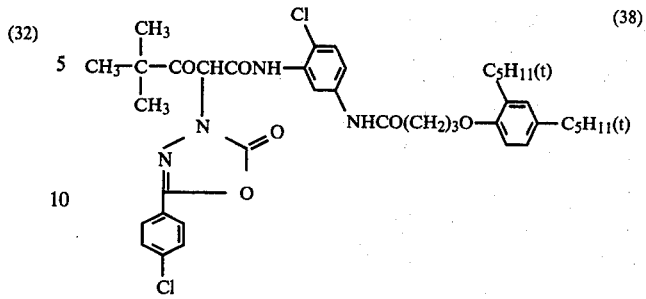 (38)
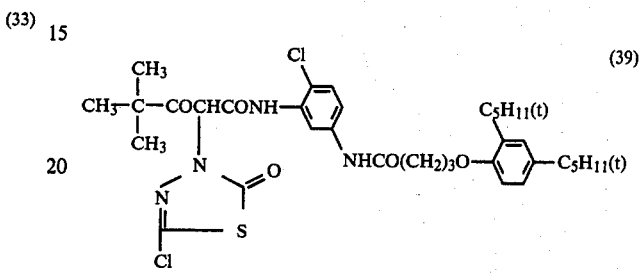 (39)
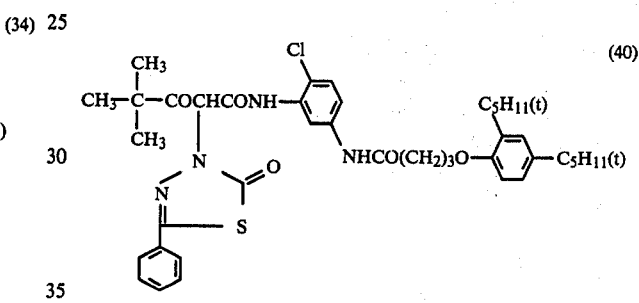 (40)
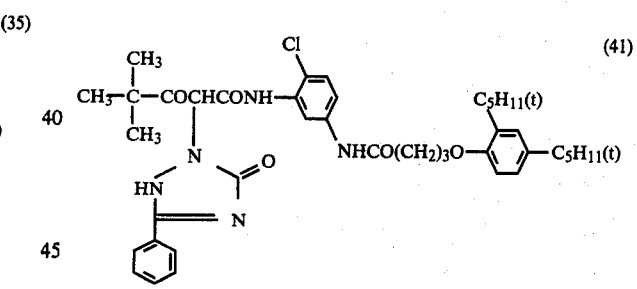 (41)
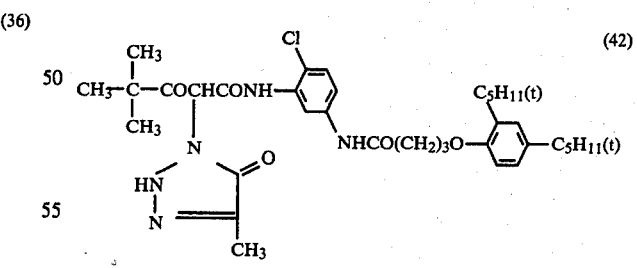 (42)
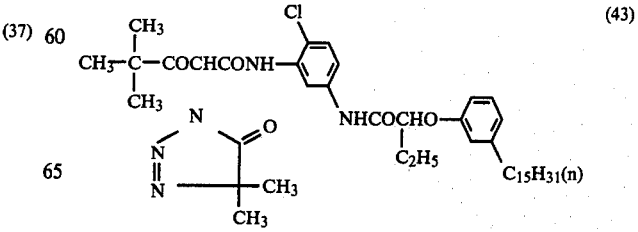 (43)

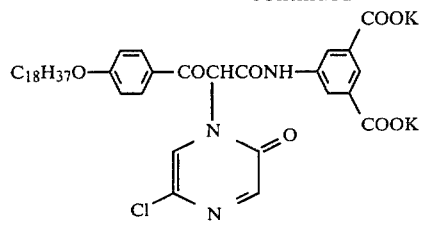
(44)
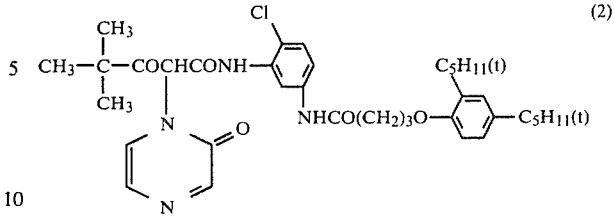
(2)
3. A process according to claim 1 wherein said
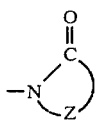
is selected from the group consisting of
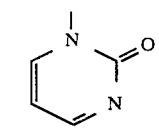 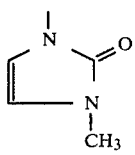 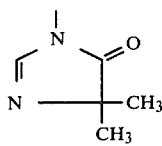
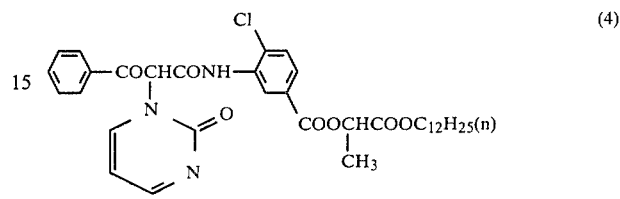
(4)
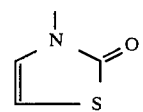 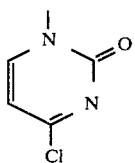 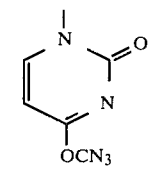
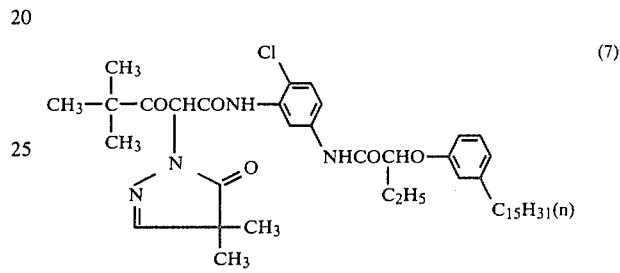
(7)
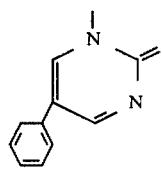 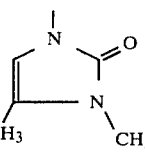 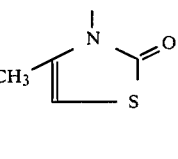
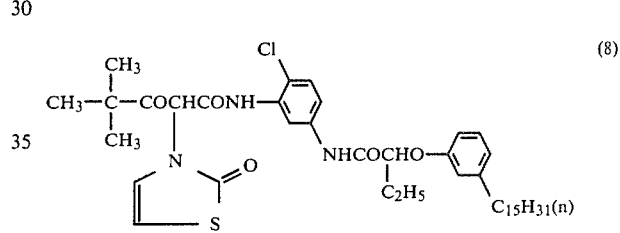
(8)
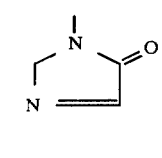 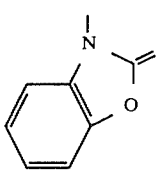 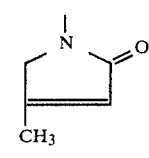
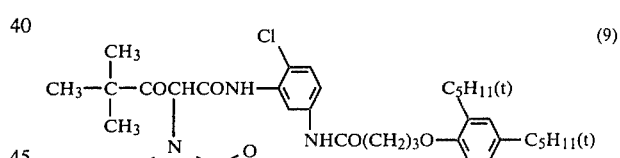
(9)
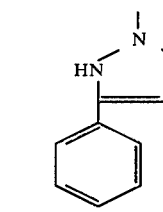  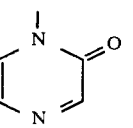
(12)
4. A process according to claim 2 wherein said yellow coupler is taken from the class consisting of
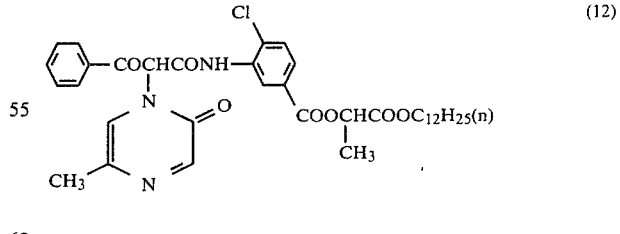
(13)

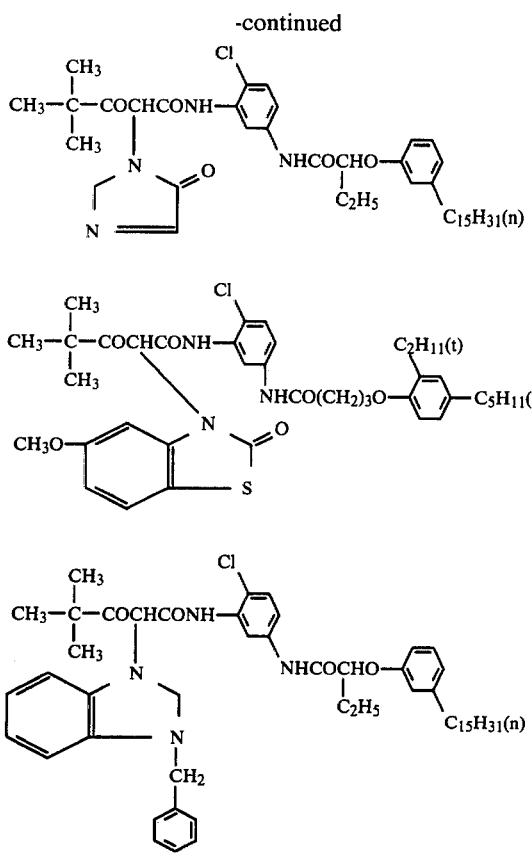
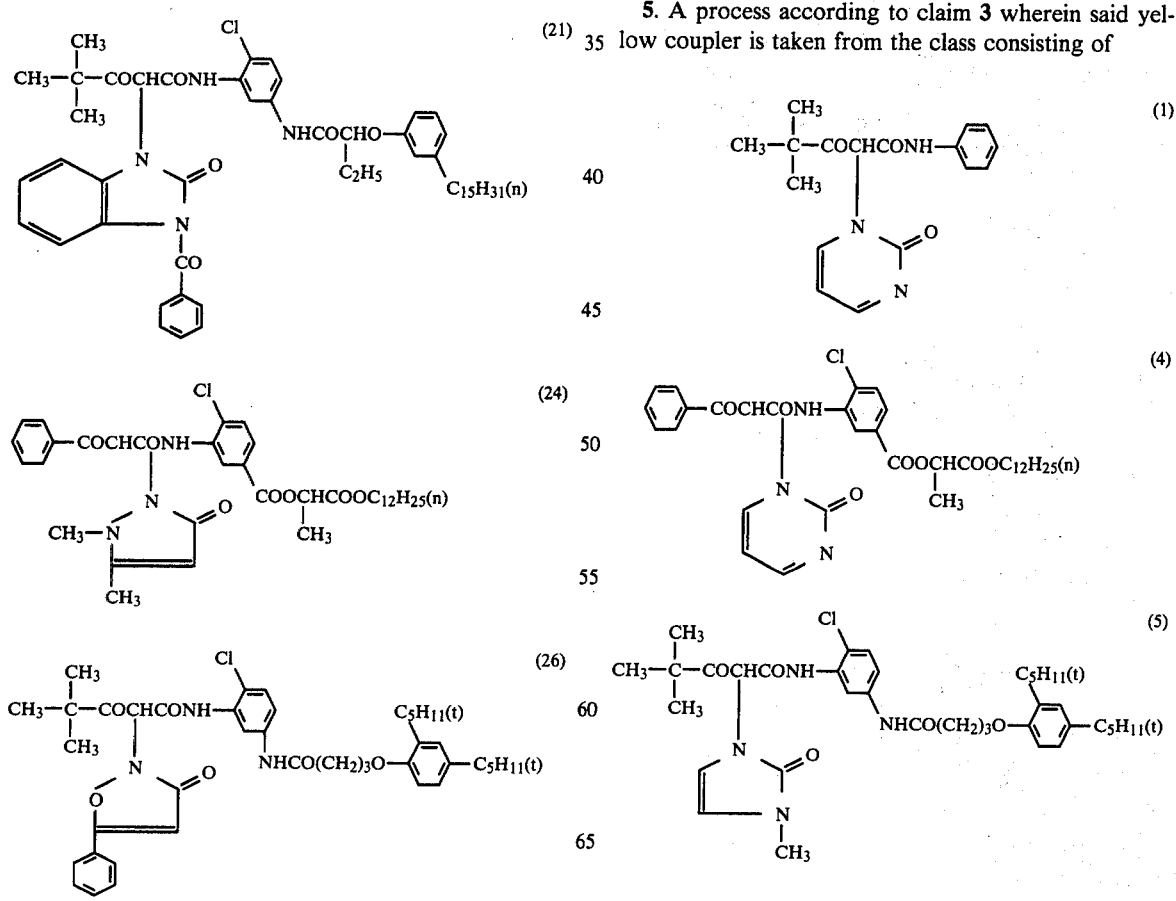
5. A process according to claim 3 wherein said yellow coupler is taken from the class consisting of -continued
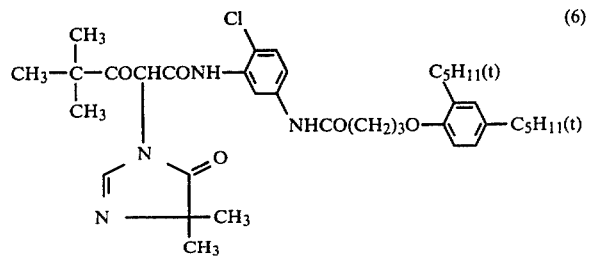 (6)
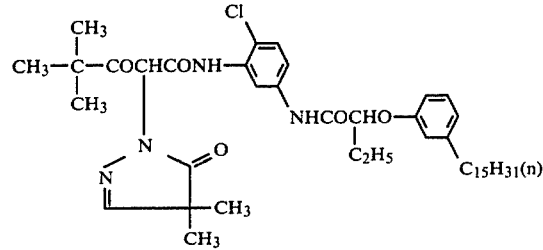 (7)
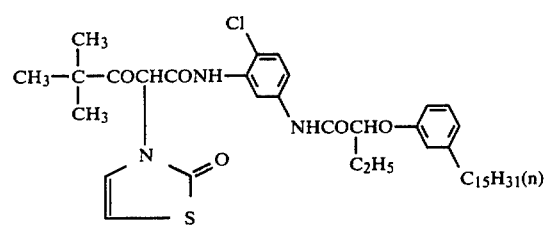 (8)
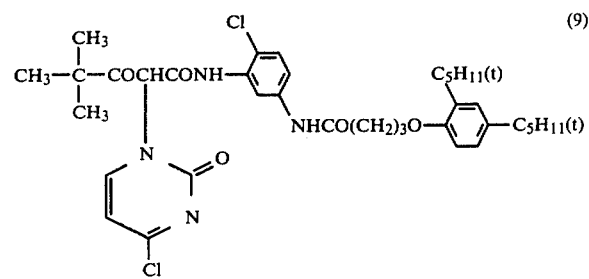 (9)
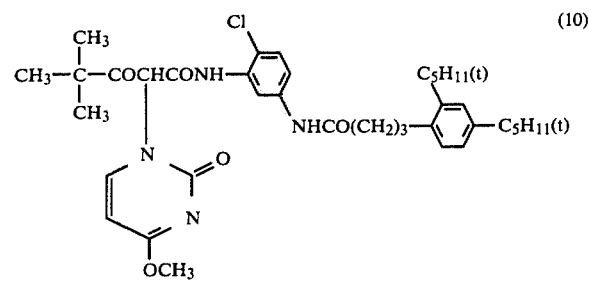 (10)
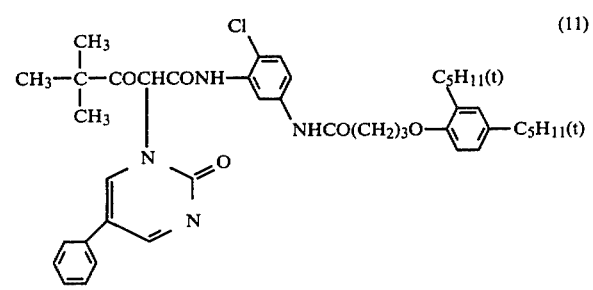 (11)
-continued
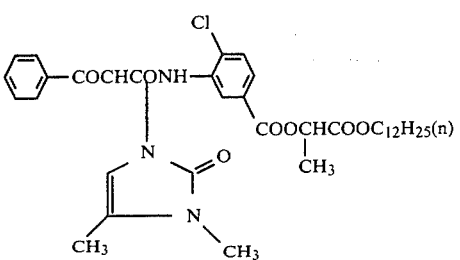 (13)
(14)
(17)
(18)
(30)
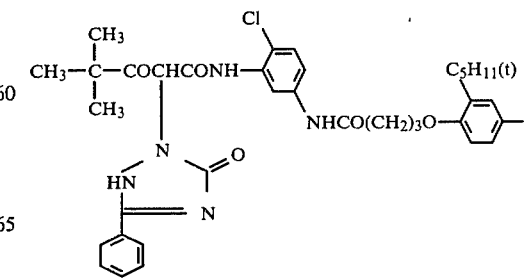 (41)

-continued

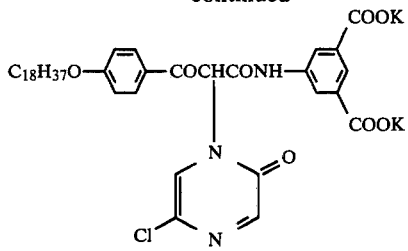
(44)

6. A process for forming a yellow color image according to claim 1 wherein the heterocyclic ring for Z is selected from the group consisting of tetrazine-one, pyrrolone, imidazolone, tetrazolone, isoxazolone, oxadiazolone, thiazolone, isothiazolone, and thiadiazolone.

7. The combination comprising a light-sensitive silver halide photographic material and the photographic yellow coupler according to claim 1.

8. The process of claim wherein said yellow coupler is present in the layer of the exposed silver halide photographic emulsion.

9. The process of claim 1 wherein said yellow coupler is present in the solution of the developer.

10. A process according to claim 6 wherein Z has at least one substituent taken from the class consisting of halogen, alkyl, alkoxy, aralkyl, aryl, aryloxy, carboxy, acyl, amino, acylamino, and a condensed ring.

* * * * *